(12) United States Patent
Shirvan et al.

(10) Patent No.: US 7,196,063 B1
(45) Date of Patent: Mar. 27, 2007

(54) PEPTIDES AND PHARMACEUTICAL COMPOSITIONS COMPRISING SAME

(75) Inventors: Anat Shirvan, Herzlia (IL); Ilan Ziv, Kfar-Sava (IL)

(73) Assignee: NST NeuroSurvival Technologies Ltd., Petach Tikva (IL)

( * ) Notice: Subject to any disclaimer, the term of this patent is extended or adjusted under 35 U.S.C. 154(b) by 370 days.

(21) Appl. No.: 10/048,955

(22) PCT Filed: Aug. 1, 2000

(86) PCT No.: PCT/IL00/00459

§ 371 (c)(1),
(2), (4) Date: Feb. 5, 2002

(87) PCT Pub. No.: WO01/18031

PCT Pub. Date: Mar. 15, 2001

(30) Foreign Application Priority Data

Aug. 5, 1999 (IL) .................................. 131266

(51) Int. Cl.
*A61K 38/00* (2006.01)
*A61K 49/00* (2006.01)
*A61K 51/00* (2006.01)

(52) U.S. Cl. .................. 514/14; 514/2; 514/12; 514/15; 514/16; 424/1.69; 424/9.1

(58) Field of Classification Search .................. 514/14, 514/2, 12, 15, 16; 424/1.69, 9.1
See application file for complete search history.

(56) References Cited

U.S. PATENT DOCUMENTS

| | | | |
|---|---|---|---|
| 3,701,433 A | 10/1972 | Krakauer et al. | |
| 3,935,111 A | 1/1976 | Bentley | |
| 4,283,289 A | 8/1981 | Meyst et al. | |
| 4,350,594 A | 9/1982 | Kawai et al. | |
| 4,572,724 A | 2/1986 | Rosenberg et al. | |
| 5,552,290 A | 9/1996 | Michelson et al. | |
| 5,567,615 A | 10/1996 | Degen et al. | |
| 5,608,060 A | 3/1997 | Axworthy et al. | |
| 5,630,946 A | 5/1997 | Hart et al. | |
| 5,630,996 A | 5/1997 | Reno et al. | |
| 5,744,047 A | 4/1998 | Gsell et al. | |
| 5,834,433 A | 11/1998 | Krstenansky | |
| 5,910,442 A | 6/1999 | Gelman | |
| 6,024,964 A | 2/2000 | Jung et al. | |
| 6,074,650 A | 6/2000 | Jung et al. | |

FOREIGN PATENT DOCUMENTS

| | | |
|---|---|---|
| EP | 0 210 412 A | 2/1987 |
| EP | 0 755 516 B1 | 1/1997 |
| IS | 125908 | 8/1998 |
| WO | WO 91/04628 | 4/1991 |
| WO | WO 95/34315 | 12/1995 |
| WO | WO 96/29403 | 9/1996 |
| WO | WO 97/01760 | 1/1997 |
| WO | WO 97/35971 | 10/1997 |
| WO | WO 97/40059 | 10/1997 |
| WO | WO 97/40070 | 10/1997 |
| WO | WO 98/05777 | 2/1998 |
| WO | WO 00/10673 | 3/2000 |
| WO | WO 01/18031 A3 | 3/2001 |

OTHER PUBLICATIONS

Halbreich et al., "*Biomedical Applications of Maghemite Ferrofluid*", May-Jun. 1998, pp. 379-390, Biochimie, 80(5-6).
Mercy Joseph et al., "*Conformations of Peptides Corresponding to Fatty Acylation Sites in Proteins*", pp. 19439-19440, Aug. 18, 1995, The Journal of Biological Chemistry, vol. 270, No. 33.
Miltenyi Biotec Inc. "*MACS Apoptotic Cell Isolation Kit*",,,251 Suburn Ravine Rd., Suite 208, Auburn CA 95603, Brochure.
Moumaris et al., "*Effect of Fatty Acid Treatment in Cerebral Malaria-Susceptible and Nonsusceptible Strains of Mice*", Dec. 1995, pp. 997-999, J. Parasitol, 81 (6).
Muchmore et al., "*X-Ray and NMR Structure of Human BCL-X, an Inhibitor of Programmed Cell Death*", May 23, 1996, pp. 335-341, Letters to Nature, vol. 381.
Sabolovic et al., "*Membrane Modifications of Red Blood Cells in Alzheimer's Disease*", Jul. 1997, pp. 217-220, J. Gerontol. A. Biol. Sci. Med. Sci., 52(4):B.
Sestier et al., "*Use of Annexin V-Ferrofluid to Enumerate Erythrocytes Damaged in Varouis Pathologies or During Storage In Vitro*", Nov. 1995, pp. 1141-1146, C R Acad Sci III, 318:11.

*Primary Examiner*—B. Dell Chism
(74) *Attorney, Agent, or Firm*—Nixon Peabody LLP; Jeffrey L. Costellia

(57) ABSTRACT

The present invention relates to an NST500 compound of general formula (I): comprising the following components: $X_1—X_2—\{(X_3)_a/X_4/X_5\}—X_6$, wherein: $X_1$ stands for a saturated or unsaturated fatty acid residue comprising 6–20 carbon atoms; or a cysteine residue bound through a thio-ether bond to a prenyl group comprising 5–20 carbon atoms; said residue being linked to the adjacent component of the compound through an amide bond; $X_2$ is 0; $X_3$ comprises 1–6 amino acids, of which 1–6 are positively charged and 0–2 are negatively charged, the other amino acid residues being polar uncharged amino acids; $X_4$ comprises 1–6 amino acids, of which 1–2 are aromatic amino acids, the other amino acids being selected among polar uncharged amino acids and hydrophobic aliphatic amino acids; $X_5$ comprises 6–8 amino acids, of which 4–6 are positively charged and 0–2 are negatively charged, the other amino acid residues being polar uncharged amino acids, wherein the amino acids form a cyclic structure; $X_6$ is a compound of general formula II, wherein Z stands for a spacer group selected among alkane and alkene containing 1–5 carbon atoms, J stands for a functional group selected among amines, thiols, alcohols, carboxylic acids and esters, aldehydes and alkyl halides; U is 0 or is selected among a labeling group; wherein a stands for an integer of 1–3; and the groups $X_3$, $X_4$ and $X_5$ being located at various places in the compound; as well as functional equivalents thereof and/or compounds having the same biological activity thereto. The present also relates to pharmaceutical compositions and methods of using the same.

30 Claims, 18 Drawing Sheets

Figure 1A:
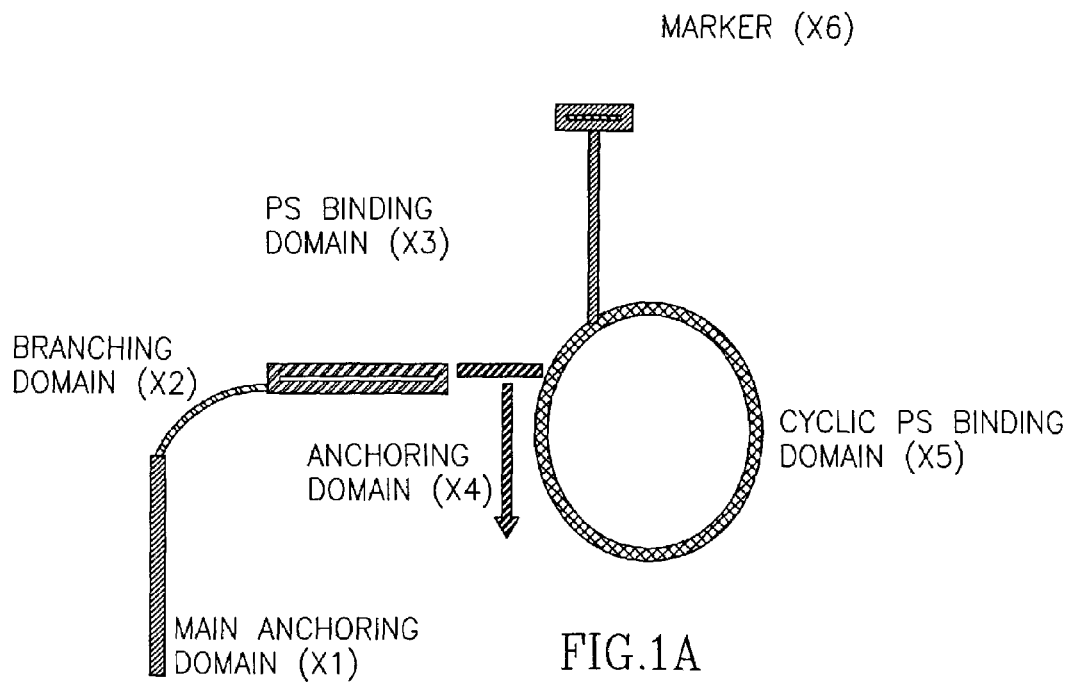

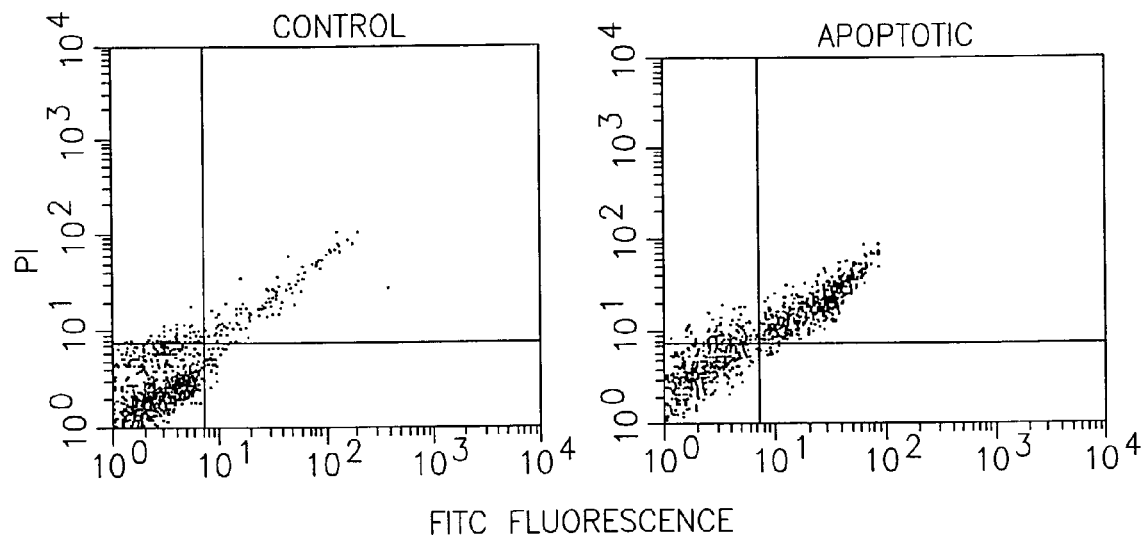
FIG.3A/1
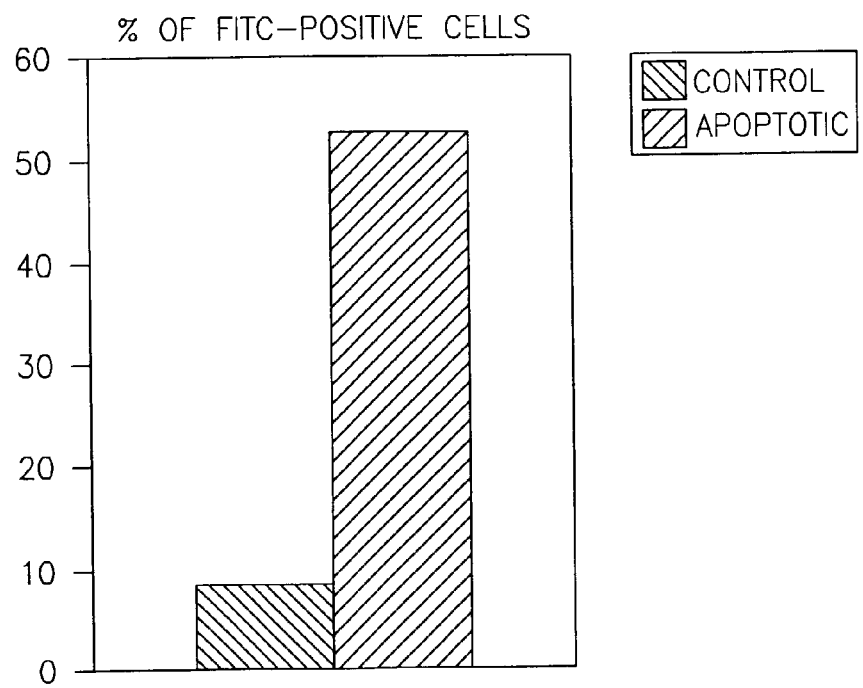
FIG.3A/2

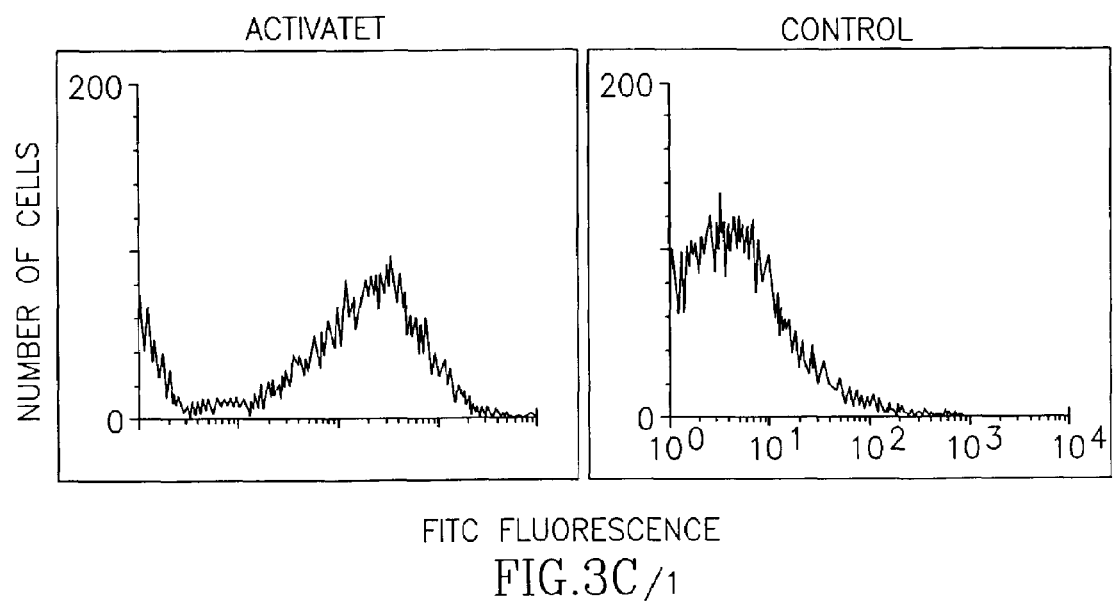
FIG.3C/1
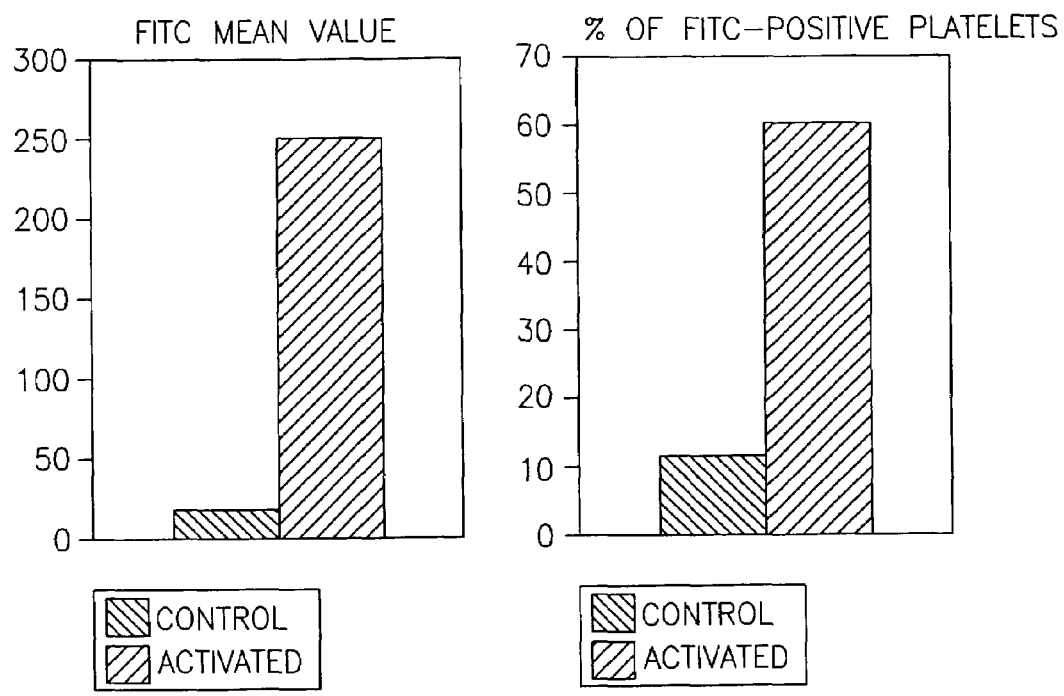
FIG.3C/2

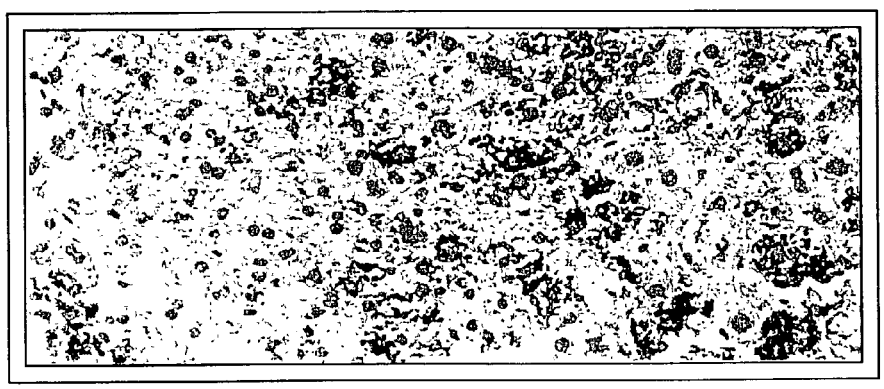
FIG.8A 20 min
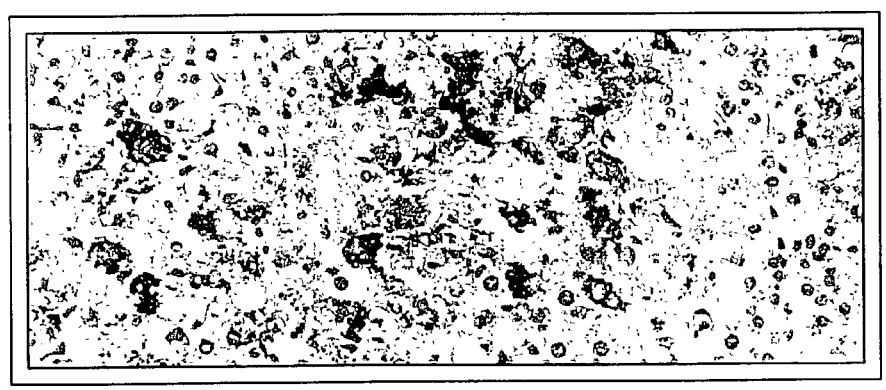
FIG.8B 60 min
FIG.8C 90 min
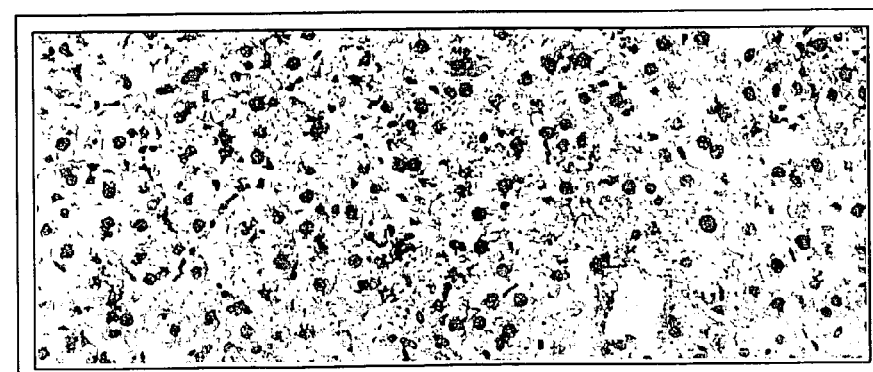
FIG.8D 120 min

PEPTIDES AND PHARMACEUTICAL COMPOSITIONS COMPRISING SAME

The present invention relates to novel compounds and pharmaceutical preparations comprising same, their use in the treatment of and in the diagnosis of certain diseases, in particular of diseases involving changes of cell membrane lipid asymmetry (CMLA).

CMLA is the phenomenon, by which normal eukaryotic cells have an asymmetrical organization of the phospholipids comprising their plasma membranes; the outer membrane leaflet is formed predominantly with the cholinephospholipids: (phosphatidylcholine [PC] and sphingomyelin), whereas the majority of the amino phospholipids (phosphatidylserine [PS] and phosphoethanolamine [PE]) are confined to the membrane's inner leaflet (Zwaal R F A & Schronit A J, Blood 1997; 89:1121–1132). The physiological importance of CMLA is exemplified by the fact that its maintenance requires a continuous, considerable investment of energy by the cell (Seigneuret M & Devaux P F, Proc. Natl. Acd. Sci., 1984; 81:3751). At least three distinct systems are active in the regulation of CMLA:

1. Aminophospholipid translocase (APT): an ATP-dependent enzyme which transports PS and PE from the outer to the inner membrane leaflet, against the concentration gradient (Daleke D L & Huestis W H, Biochemistry 1985; 24:5406).

2. ATP-dependent floppase: transports amino-phospholipids and cholinephospholipids from the inner to the outer leaflet. This enzyme is tenfold slower than APT (Andrick C et al., Biochim. Biophys. Acta 1991; 1064:235).

3. Lipid scramblase: A potent, $Ca^{2+}$-dependent and ATP-independent enzyme, that rapidly moves phospholipids back and forth between the two membrane leaflets (flip-flop), leading within minutes to loss of CMLA (Zwaal R F A & Schronit A J, Blood 1997; 89:1121–1132).

In addition, other factors, such as membrane anchoring of cytoskeletal proteins have been suggested to assist in CMLA maintenance.

Whereas the maintenance of CMLA is fundamental to normal cell physiology, its loss, with subsequent surface exposure of PS plays a role in numerous states of both physiological and pathological characters. The surface exposure of anionic phospholipids plays an indispensable role in the formation of a catalytic surface for the assembly of several clotting factor complexes. Thus, the loss of CMLA in activated platelets as well as in other cell types (e.g. endothelial cells), is an important factor in normal blood coagulation. However, CMLA loss also assists in the initiation and/or propagation of abnormal, excessive blood clotting in numerous disorders. These disorders include, among others:

1. Arterial or venous thrombosis (Thiagarajan P & Benedict C R, Circulation 1997; 96:2339–2347; Van Ryn McKenna J, et al., Throm. Hemost. 1993; 69:227–230).

2. Sickle cell disease (Tait J F & Gibson D, J. Lab. Clin. Med. 1994; 123:741).

3. Beta-thalassemia (Borenstein-Ben-Yashar Y, et al., Am. J. Hematol. 1994; 47:295; Ruf A, et al., Br. J. Haematol. 1997; 98:51–56).

4. Antiphospholipid antibody syndrome; among others in systemic lupus erythematosus. Lack of CMLA has been specifically linked to the recurrent abortions associated with said syndrome (Rand J H, et al., N. Engl. J. Med. 1997; 337:154–160).

5. Shed membrane microparticles, e.g., during cardiopulmonary bypass, (Nieuwland R et al., Circulation 1997; 96:3534–3541; Aupeix K, et al., J. Clin. Invest. 1997; 99:1546–155).

6. Urolithiasis (Bigelow M. W. et al, 19)

Apoptosis is another major situation in which CMLA loss takes place. Apoptosis is an intrinsic program of cell self-destruction or "suicide", which is inherent in every eukaryotic cell. In response to a triggering stimulus, cells undergo a highly characteristic cascade of events of cell shrinkage, blebbing of cell membranes, chromatin condensation and fragmentation, culminating in cell conversion to clusters of membrane-bound particles (apoptotic bodies), which are thereafter engulfed by macrophages (Boobis A R, et al., Trends Pharmacol. Sci. 10:275–280, 1989; Bursch W, et al., Trends Pharmacol. Sci. 13:245–251, 1992). Loss of CMLA is quite a universal phenomenon in apoptosis (Van den Eijnde S M, et al., Cell death Diff. 1997; 4:311–316). Loss of CMLA occurs early in the apoptotic cascade, immediately following the point of cell commitment to the death process (Van-Engeland M, et al., Cytometry 1998; 31:1–9; Martin S J, et al., J. Exp. Med. 1995; 182:1545–1556). It has also been shown that the loss of CMLA is an important factor in the recognition and removal of apoptotic cells by macrophages (Balasubramanian K, et al., J. Biol. Chem. 1997; 272: 31113–31117). A strong correlation has recently been drawn between the loss of CMLA and the potent pro-coagulant activity of apoptotic cells (Bombeli T, et al., Blood 1997; 89:2429–2442; Flynn P D, et al., Blood 1997; 89:4378–4384). The latter activity in apoptotic endothelial cells, such as those recently recognized in atherosclerotic plaques (Kockx M M, et al., Circulation 1998; 97:2307–2315, Mallat Z, et al., Circulation 1997; 96:424–428), probably plays an important role in the pathogenesis of thrombotic vascular disorders.

The diagnosis of the loss of CMLA may therefore serve as an important tool for the detection of cell death, specifically by apoptosis. A method for the detection of cell death may have many applications, both as a diagnostic tool and as a method to monitor the disease course in numerous disorders associated with impairment of tissue homeostasis. Among these applications are:

1. Monitoring of a response to anti-cancer therapy:

Currently there is a lag period between the time of administration of anticancer drugs and the time of evaluation of their efficacy. Thus, in case of failure of a therapeutic regimen, this lag time may be hazardous to the patient in two aspects:

a. loss of precious time without an effective therapy; and b. unnecessary exposure of the patient to drug adverse effects.

Therefore, there is clearly a need for an early detection of tumor response to treatment. Since anti-tumor drugs exert their effects by induction of apoptosis (Eastman A, Cancer Cells, 1990; 2:275–280), the detection of apoptosis, potentially by detection of CMLA loss may be useful for monitoring tumor response.

2. Diagnosis of disorders of inappropriate excessive apoptosis. These disorders include, among others, AIDS, neurodegenerative disorders, myelodysplastic syndromes and various ischemic or toxic insults (Thompson C B, Science 1995; 267:1456–1461).

3. Monitoring of graft survival following organ transplantation. The increasing use of organ transplantation for the treatment of end-stage organ failure emphasizes the need for the development of methods for sensitive monitoring of graft survival. Apoptosis plays a major role in graft cell loss (Matsuno T, et al., Transplant Proc. 1996; 28:1226–1227; Dong C et al., Lab. Invest. 1996; 74:921–931).

4. Monitoring of response to cytoprotective treatments. The current intensive research of cytoprotective agents, towards development of drugs capable of inhibiting cell loss in various diseases (Thompson C B, Science 1995; 267: 1456–1461), dictates a need for measures to evaluate the effects of such compounds, i.e., monitoring of cell death, in all levels of research, from in vitro tissue culture studies, through in vivo animal models to human clinical studies.

5. Basic research of apoptosis in tissue cultures and animal models.

The loss of the normal CMLA has, as indicated above, wide implications for various pathophysiological states. A compound capable of selectively binding to membranes upon CMLA loss, thus serving as a marker for this phenomenon, may therefore have wide diagnostic applications. Moreover, by shielding the exposed anionic phospholipids, specifically PS, such compound may be a useful therapeutic agent, for example for the above-mentioned disorders, which are associated with excessive pro-coagulant activity caused by the membrane phospholipid re-organization.

In addition, a compound capable of detecting cells undergoing apoptosis may have important applications for targeting drugs to apotosis-inflicted tissues. Apotosis and its major control systems are shared by all tissues in the body. Therefore, the implementation of the emerging new generation of drugs, active by modulation of apotosis control is expected to depend, at least in part, on the ability to target these drugs to the appropriate tissues. An apoptosis-detecting compound may thus be useful for this task.

There have been developed certain measures for the effective detection of cell death in tissue cultures, such as the TUNEL (terminal deoxynucleotidyl transferase-mediated dUTP-biotin end-labeling) method, for the detection of the characteristic chromatin cleavage of apoptotic cells. However, this method, as well as other methods such as the DNA laddering method, are strictly limited to the in vitro level.

The potential of a detector of CMLA loss both as a diagnostic tool and as a therapeutic measure has recently been exemplified by the use of annexin-V for these indications. Annexin V is a member of the annexin family of proteins, sharing potent, $Ca^{2+}$-dependent binding to anionic phospholipid membranes (Swairjo M A, et al., Nature Struc. Biol. 1995; 968–974) . Annexin V is a 320 amino acid protein, with a molecular mass of 35,935 daltons (Huber R, et al., EMBO J. 1990; 9:3867–3874). Though the physiological role of annexin-V has not been fully elucidated, it has been suggested to be involved in anticoagulation, anti-inflammation and cellular signaling (Romisch J, et al., Thromb. Res. 1990; 60:355–366; Bastian B C, J. Invest. Dermatol. 1993; 101:359–363; Kaneko N, et al., J. Mol. Biol. 1997; 274:16–20). The impressive affinity of annexin V to anionic phospholipid membranes (Kd of about $10^{-9}$–$10^{-11}$M, [Hofmann A, et al., Biochim. Biophys. Acta, 1997; 254–2641) has been extensively utilized for both the diagnosis of CMLA loss and modulation of disorders associated with this phenomenon. Fluorescein isothiocyanate (FITC)-labeled annexin V has been widely used for the detection of apoptosis in various tissue culture models (Koopman G, et al., Blood 1994; 84:1415–1420; Rimon G, et al., J Neurosci Res 1997; 48:563–570; Van-Engeland M, et al., Cytometry 1998; 31:1–8). Preliminary successful studies were also performed with systemic intracardial injection of biotinylated annexin V to viable mouse embryos, for the detection of developmentally-associated apoptosis (Van den Eijnde S M, et al., Cell death Diff. 1997; 4:311–316).

Systemic administration of $^{99m}$Tc-annexin V was also used to detect and image cell death in several models in vivo, e.g. fulminant hepatitis in mice, acute rejection of transplanted cardiac allograft in rats and monitoring of response of lymphoma to cyclophosphamide treatment in mice (Blankenberg F G. et. al. Proc. Natl. Acad. Sci. USA, 95:6349–6354, 1998). $^{125}$I-labeled annexin V was also used for in vivo detection of thrombosis in an animal model (Stratton J R, et al., Circulation 1995; 92:3113–3121). Inhibition of arterial thrombosis was effectively achieved by intravenous administration of annexin V in a carotid artery injury model (Thiagarajan P & Benedict C R, Circulation 1997; 96:2339–2347). Annexin V is also known as diagnostic agent (U.S. Pat. No. 5,627,036).

However, the use of annexin V as a drug or as a diagnostic probe is rendered problematic by several characteristics of this protein. Annexin V is a protein of considerable size, a factor which may substantially limit its volume of distribution in the body. Moreover, it is active as a potent membrane-binding protein only if allowed to form a highly organized multimer on the membrane surface (Concha N O, et al., FEBS Lett 1992; 314:159–162; Voges D, et al., J. Mol. Biol. 1994; 238:199–213, Andree H A M, et a., J. Biol. Chem 1992; 267:17907–17912). Thus, systemic administration of annexin V as a drug is expected to be associated with rapid degradation and loss of the function of the administered protein. Indeed, a very rapid clearance (90% within 5 minutes) was observed in rabbits following intravenous injection of annexin V (Thiagarajan P & Benedict C R, Circulation 1997; 96:2339–2347). In addition, the administration of annexin V may induce an untoward immunological response. Importantly, anti-annexin V antibodies have been recently implicated in the pathogenesis of anti-phospholipid antibody syndrome and associated thrombotic events (Nakamura N, et al., Am. J. Hematol. 1995; 49:347–348; Kaburaki J & Ikeda Y, Rinsho Ketsueki 1995; 36:320–324, Rand J H, et al., N. Engl. J. Med. 1997; 337:154–160).

Co-pending IL patent application No. 125908 describes and claims

A NST300 compound (as herein defined) of general formula I: comprising the following components:

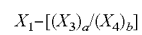

wherein:

X$_1$ stands for a saturated or unsaturated fatty acid residue comprising 6–20 carbon atoms; or a cysteine residue bound through a thioether bond to a prenyl group comprising 5–20 carbon atoms; said residue being linked to the adjacent component of the compound through an amide bond;

X$_3$ comprises 1–6 amino acids, of which 1–6 are positively charged, the other amino acid residues being polar uncharged amino acids; and X$_4$ comprises 1–6 amino acids, of which 1–2 are aromatic amino acids, the other amino acids being selected among polar uncharged amino acids and hydrophobic amino acids;

wherein:

a stands for an integer of 1–8; and b stands for an integer of 1–8;

the groups X$_3$ and X$_4$ being located at various places in the compound;

as well as functional equivalents thereof.

In particular said patent application describes and claims compounds of general formula Ia

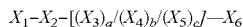

wherein:
X$_1$, X$_3$ and X$_4$ have the same meaning as above,
X$_2$ is selected among 0–3 glycine residues and 0–2 β-amino alanine molecules;
X$_5$ is a compound of general formula II

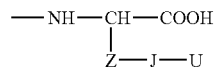

wherein Z stands for a spacer group selected among alkane and alkene containing 1–4 carbon atoms, J stands for a functional group selected among amines, thiols, alcohols, carboxylic acids, esters aldehydes and alkyl halides; U is a labeling group;
c standing for 0–10; and
X$_6$ being 0; or being selected among X$_1$ (as hereinbefore defined);
within the subunit [(X$_3$)$_a$/(X$_4$)$_b$/(X$_5$)$_c$] the groups X$_3$, X$_4$ and X$_5$ being located at various suitable places;
as well as functional equivalents thereof.

Further, said application claims a process for the preparation of said compounds, pharmaceutical preparations and a diagnostic kit comprising same, the use of said compounds and methods for targeting drugs using said compounds.

Co-pending U.S. patent application Ser. No. 09/200,715, filed on 27 Nov., 1998 describes and claims an affinity filter effective in capturing and thereby removing particles characterized by surface exposure of anionic phospholipids present in blood or blood-derived products, the affinity filter comprising a body containing a solid support and an anionic-phospholipid binding compound linked to said solid support, said anionic-phospholipid binding compound being for specifically binding the particles characterized by surface exposure of anionic phospholipids and thereby removing the particles from the blood or blood-derived products.

Furthermore, said patent claims a method of capturing and thereby removing particles characterized by surface exposure of anionic phospholipids present in blood or blood-derived products comprising the step of directing the blood or blood-derived products through an affinity filter including a body containing a solid support and an anionic-phospholipid binding compound linked to said solid support, said anionic-phospholipid binding compound being for specifically binding the particles characterized by surface exposure of anionic phospholipids and thereby removing particles from the blood or blood-derived products.

In said U.S. patent specification there are mentioned and claimed as anionic binding compounds being part of said filter, for example, annexin and NST300 compounds.

However, the NST300 compounds are not always satisfactory as this is often the case with pharmaceutically effective compounds.

Thus, it was desirable to develop further novel compounds, for the diagnosis of CMLA loss, the modulation of its pathophysiological consequences and for the treatment of certain diseases in which said CMLA loss plays a role, and for use as anionic phospholipid binding compound linked to solid support in order to remove particles from blood or blood derived products.

The present invention thus consists in a compound (hereinafter: "NST500 compound") of general formula I comprising the following components:

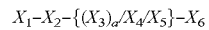

wherein:
X$_1$ stands for a saturated or unsaturated fatty acid residue comprising 6–20 carbon atoms; or a cysteine residue bound through a thioether bond to a prenyl group comprising 5–20 carbon atoms; said residue being linked to the adjacent component of the compound through an amide bond;
X$_2$ is either 0 or consists of a unit of general formula A*2$^n$, in which A stands for a branching unit and n stands for 0–4;
X$_3$ comprises 1–6 amino acids, of which 1–6 are positively charged and 0–2 are negatively charged, the other amino acid residues being polar uncharged amino acids;
X$_4$ comprises 1–6 amino acids, of which 1–2 are aromatic amino acids, the other amino acids being selected among polar uncharged amino acids and hydrophobic aliphatic amino acids;
X$_5$ comprises 1–6 amino acids, of which 1–6 are positively charged and 0–2 are negatively charged, the other amino acid residues being polar uncharged amino acids, wherein the amino acids have a cyclic structure;
X$_6$ is a compound of general formula II

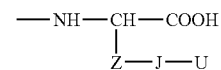

wherein Z stands for a spacer group selected among alkane and alkene containing 1–5 carbon atoms, J stands for a functional group selected among amines, thiols, alcohols, carboxylic acids and esters, aldehydes and alkyl halides; U is either 0 or is selected among a labeling group;
wherein:
a stands for an integer of 1–3; and
the groups X$_3$, X$_4$ and X$_5$ being located at various places in the compound;
as well as functional equivalents thereof and/or compounds having the same biological activity thereto.

For the sake of clarity it should be indicated that the term "prenyl" herein stands also for the term "isoprenyl" (see Stedman's Medical Dictionary, Baltimore, USA, William and Wilkins, eds., 1990:565, 1253).

X$_1$ serves as main anchoring domain;
X$_2$, if present, serves as branching domain;
X$_3$ serves as anionic phospholipid binding determinant;
X$_4$ serves as accessory anchoring domain;
X$_5$ serves as anionic phospholipid binding domain bearing a cyclic conformation; and
X$_6$ serves as a labeling domain.

X$_1$ is advantageously a residue of a saturated fatty acid of formula $CH_3(CH_2)_nCO_2H$, in which n stands for an integer of 8–18 preferably selected among myristic acid and palmitic acid; or X$_1$ is advantageously a cysteine residue bound through a thioether bond to a prenyl of 5–15 carbon atoms, preferably farnesyl cysteine.

Branching unit A of X$_2$ is advantageously selected among a di-carboxylic or a poly-carboxylic acid.

The positively charged amino acids of $X_3$ and $X_5$ are advantageously selected among lysine, arginine, histidine or any amino acid which is comprised of a positively charged group, e.g. primary amine, secondary amine, guanidine, covalently bound to the α-carbon atom or to the α-amine on the peptide backbone by a spacer comprised of an alkene of 1–4 carbon atoms; and combinations thereof. The acids are preferably selected among lysine and arginine and combinations thereof. The negatively charged amino acids of $X_3$ and $X_5$ are preferably selected among glutamate and aspartate. The polar uncharged amino acids of $X_3$, and $X_5$ are preferably selected among serine, threonine, asparagine and glutamine and combinations thereof.

The aromatic amino acids of $X_4$ are preferably selected among phenylalanine and tryptophan and combinations thereof; the polar uncharged amino acids are preferably selected among serine, asparagine and glutamine and combinations thereof; and the hydrophobic aliphatic amino acids are preferably selected among leucine, valine, alanine and glycine and combinations thereof.

The cyclization in $X_5$ may be performed via an intramolecular di-sulfide bridge, by an amide bond or via a coordination bond to a metal, preferably to $^{99}$Tc, that may serve also as a marker.

U as a labeling group for specific binding is advantageously selected among biotin and a group containing a substituent selected among a fluorescein, a radioisotope and a paramagnetic contrast agent; the fluorescein may be, for example, fluorescein isothiocyanate; the radioisotope may be selected among technetium, lead, mercury, thallium and indium; and the paramagnetic contrast agent may be any paramagnetic metal ion chelate, e.g. gadolinium-diethylenetriaminepentaacetic acid (Gd-DTPA)].

$X_6$ is advantageously a lysine residue substituted at the ε-amino group by a labeling group U as above defined.

In case that $X_6$ stands for a cysteine residue bound through a thioether bond to a prenyl group the cysteine carboxyl group can be either free or methylated.

Any of the above amino acids may be the L-, the D- or the DL isomer or the racemate.

The amino acid residues may also be residues of suitable synthetic amino acids.

One sequence of the compounds of general formulae I is:
Myristate-KVSFFCKNKEKKC-K (SEQ ID NO:1) U, in which K=lysine, V=Valine, S=serine, F=phenylalanine, C=Cysteine, N=asparagine E=Glutamic acid and U as hereinbefore defined.

A preferred compound of said sequence is:
Myristate-KVSFFCKNKEKKC-K (SEQ ID NO:1) (biotin) in which the two cystein residues are linked via a disulfide bond, to form a cyclic structure.

Figure 1B:
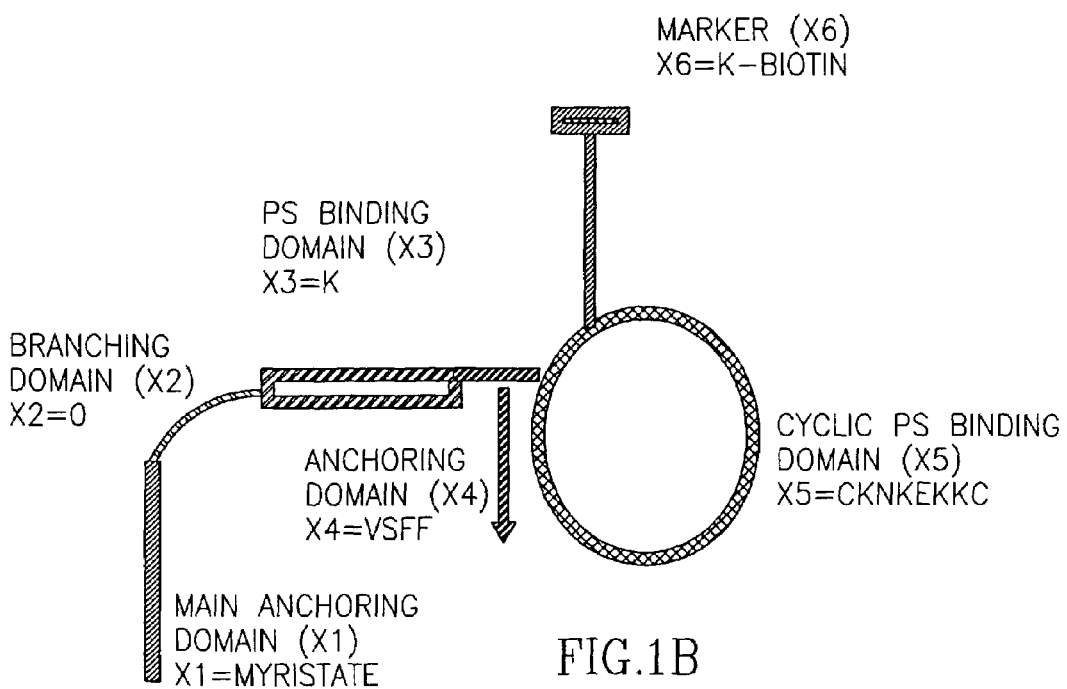

(This compound is herein called "NST513" and is described in FIG. 1b as general formula IA)

A further sequence of the compounds of general formulae I is:
Myristate-KKVSFFCKNKEKKC-K(SEQ ID NO:2)U, wherein K, V, S, F, C, N, E and U have the same meaning as above.

A preferred compound of said sequence is:
Myristate-KKVSFFCKNKEKKC-K(SEQ ID NO:2) (biotin) wherein the two cystein residues are linked together to form a cyclic structure.

Figure 1C:
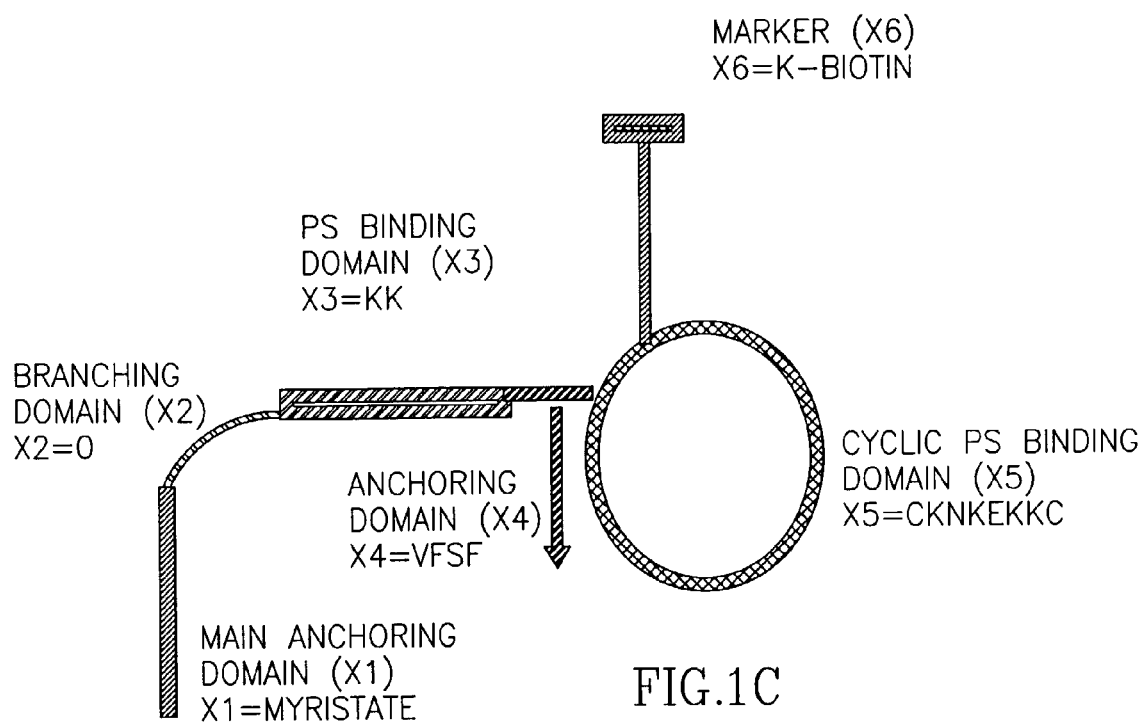
Figure 1D:
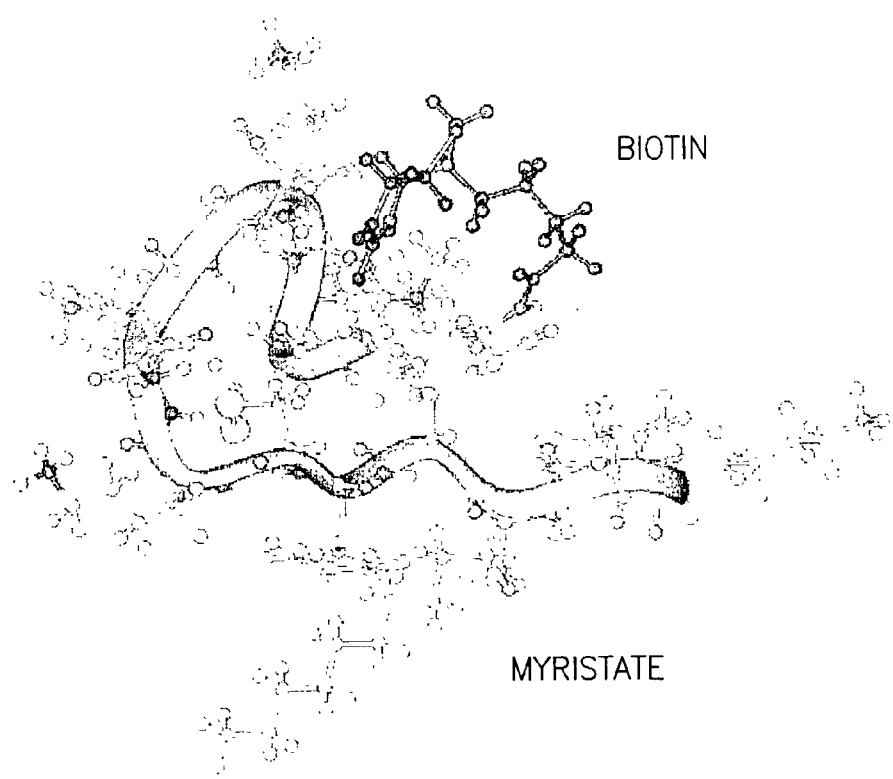

(This compound is herein called "NST516" and is described in FIG. 1c as general formula IB)

The present invention also consists in pharmaceutical compositions comprising as active ingredient a NST500 compound as defined above with reference to general formulae I.

In a preferred embodiment the pharmaceutical composition comprises in addition to the NST500 compound a pharmaceutically acceptable carrier.

The carriers may be selected among any suitable components, e.g. solvents; emulgators; excipients; talc; flavors; colors; etc. The pharmaceutical composition may comprise, if desired, also other pharmaceutically active compounds. The pharmaceutical compositions may be, e.g. tablets, capsules, solutions, emulsions, etc.

The pharmaceutical composition according to the present invention may comprise an additional pharmaceutically active compound.

The amount of the NST500 compound incorporated in the pharmaceutical composition may vary widely. The factors which have to be considered when determining the precise amount are known to those skilled in the art. Such factors include, inter alia, the pharmaceutical carrier being part of the composition, the route of administration being employed and the frequency with which the composition is to be administered.

The pharmaceutical composition may be administered by any of the known methods, inter alia, per os, intravenous, intrapertional, intramuscular or subcutaneous or topical administration.

The present invention further consists in the use of a NST500 compound or of a pharmaceutical composition comprising same in the preparation of a medicament, in particular for the treatment or prevention of prothrombotic states; advantageously for the treatment of disorders which are associated with excessive pro-coagulant activity, initiated or propagated by CMLA loss, such as arterial or venous thrombosis; sickle cell disease; thalassemia; antiphospholipid antibody syndrome; systemic lupus erythematosus (SLE); shed membrane particles, (e.g. during cardiopulmonary bypass); formation of kidney stones; apoptosis, etc.

The present invention also consists in a method for the treatment or prevention of prothrombotic states; advantageously for the treatment of disorders which are associated with excessive pro-coagulant activity, initiated or propagated by CMLA loss, such as arterial or venous thrombosis; sickle cell disease; thalassemia; antiphospholipid antibody syndrome; SLE; shed membrane particles, (e.g. during cardiopulmonary bypass); formation of kidney stones; apoptosis, etc. by a NST500 compound or by a pharmaceutical composition comprising same.

The present invention also consists in the use of a NST500 compound or of a pharmaceutical composition comprising same for the diagnosis of CMLA loss. Said use may be performed either in vitro or in vivo in accordance with the specific requirements. Said uses are especially:

a. use as a diagnostic agent for the detection and imaging of cell death, particularly of apoptosis, either in vitro or in vivo. The in vitro imaging is preferably performed with fluorescin; the in vivo imaging is preferably performed by a scan with an isotope or by MRI;

b. use as a diagnostic agent for thrombosis or for prothrombotic states; and c. use as a diagnostic agent for pathophysiological states associated with apoptosis; e.g. monitoring of response to anticancer treatments, diagnosis of disorders of inappropriate excessive apoptosis, monitoring of response to cytoprotective treatments, monitoring of graft survival following organ transplantation.

The present invention also consists in a diagnostic kit comprising a NST500 compound or a pharmaceutical comprising same for the performance of the diagnostic steps.

The present invention also consists in the use of a NST500 compound or of a pharmaceutical composition comprising same as a targeting agent, to target drugs to tissues inflicted by CMLA loss, preferably tissues the cells of which are inflicted by excessive apoptosis, or tissues in which thrombosis in association with CMLA loss takes place.

The present invention also consists in a method for targeting drugs to tissues in the body which are inflicted by CMLA loss, which method comprises the conjugation of a NST500 compound or a pharmaceutical composition comprising same with a drug to be targeted through an esteric, an amidic or the like bond. The NST500 compound directs the conjugate to regions of CMLA loss. Subsequently, naturally-occurring cleavage of the esteric bond by local tissue esterases allows the liberation of the targeted drug to act in said region. The tissues are in particular those tissues the cells of which are inflicted by excessive apoptosis or tissues in which thrombosis in association with CMLA loss takes place.

The present invention also consists in the use of NST500 compounds or of pharmaceutical compositions comprising same for basic research, in fields of research in which CMLA loss takes place, both in vitro and in viva, inter alia, of cell cultures, preferably in basic research of apoptosis or evaluation of progression or recession of apoptotic-related diseases in animal models used for basic research.

Furthermore, the present invention consists in an anionic phospholipid being a NST500 compound being part of an affinity filter effective in capturing and thereby removing particles by surface exposure of said anionic phospholipids present in blood or blood-derived products and in the use of said affinity filter.

Furthermore, the present invention consists in a method of capturing and thereby removing particles characterized by surface exposure of anionic phospholipids present in blood or blood-derived products comprising the step of directing the blood or blood-derived products through an affinity filter including a body containing a solid support and NST500 compound linked to said solid support, said NST500 compound being for specifically binding the particles characterized by surface exposure of anionic phospholipids and thereby removing particles from the blood or blood-derived products.

Moreover, the present invention further consists in a process for the preparation of a NST500 compound of general formula I by the following steps:
  a. an orthogonally protected diaminoacid is loaded on a solid support, the ω-amino protecting group is then removed, thereafter a compound comprising substituent U being a labeling agent and not standing for 0, e.g. biotin is introduced into the amino acid resin in the presence of a coupling reagent and a base, or by using a pre-activation method, then removing the α-amino protecting group of the N-terminal amino acid and the peptide being prepared sequentially on the solid support; and, if desired,
  b. a substituent $X_1$ which has the meaning given above, e.g. myristic acid, is introduced into the peptide-resin under similar conditions to those used during the coupling of the amino acids in step a and then, the peptide is cleaved from the solid support.

The peptide obtained is then advantageously purified and characterized preferably using high performance liquid chromatography—mass spectra (HPLC/MS).

The coupling method may be performed by the formation of an ester, azide or an anhydride.

The cyclization of the peptide, if desired, is performed via an intramolecular di-sulphide bridge by iodine treatment, removal of S-Acm protecting groups on the, e.g. cysteine residues ($CH_2$—S) with mercury acetate followed by air oxidation, or by simultaneous de-protection/oxidation with TI $(TFA)_3$.

The cyclization of the peptide may also be carried out by an amide bond which is formed either while the peptide is still attached to the resin, or in solution, as follows:

an amine and a carboxyl side chain being protected by groups selected among Fmoc, Ofm, allyl and Alloc protecting groups during the synthesis are reacted with an appropriate coupling agent.

The protecting groups are then removed and an amide bond is formed using an appropriate coupling method. Then, if the reaction is performed while the peptide is still attached to the resin, the peptide obtained is cleaved from the resin, purified, lyophilized and characterized preferably by HPLC/MS.

The branched 2, 4, 8 or 16 multivalent peptide, if desired, may be prepared as follows:

For a bivalent peptide a P-A is coupled with two equivalents of peptide, wherein A is an amino dicarboxylic acid and P is the protecting group of the amino group. Then the protecting groups are removed and the divalent peptide is characterized by HPLC/MS.

For a tetravalent peptide the fatty acid is coupled to A-$Y_2$, wherein Y is a protecting group of the carboxyl group. The Y protecting group is then removed and the fatty acid-A is coupled with two equivalents of A-$Y_2$, The Y group being then removed and the skeleton obtained being then coupled with a protected peptide prepared on a solid support, advantageously being a 2-chlorotrityl resin. The final skeleton peptide is advantageously purified as described above to form the tetravalent branched peptide. Lyophilized and characterizationed, preferably by HPLC/MS, are then performed.

If higher valencies are required the following extra step should be added:

The fatty acid

is then coupled with two equivalents of A—$(Y)_2$ and then the Y protecting groups are removed. Then the-skeleton is coupled with four equivalents of A—$(Y)_2$ and the process is continued as described above to form an octavalent peptide.

The sixteen valent peptide is being prepared in an analogous manner.

The present invention will now be illustrated with reference to the following accompanying Figs. and the Examples without being limited by same. In said Figs. and Examples compound NST512 is the linear compound corresponding to compound NST513 and is brought for comparative purposes.

FIGURE LIST

Figure 3B:
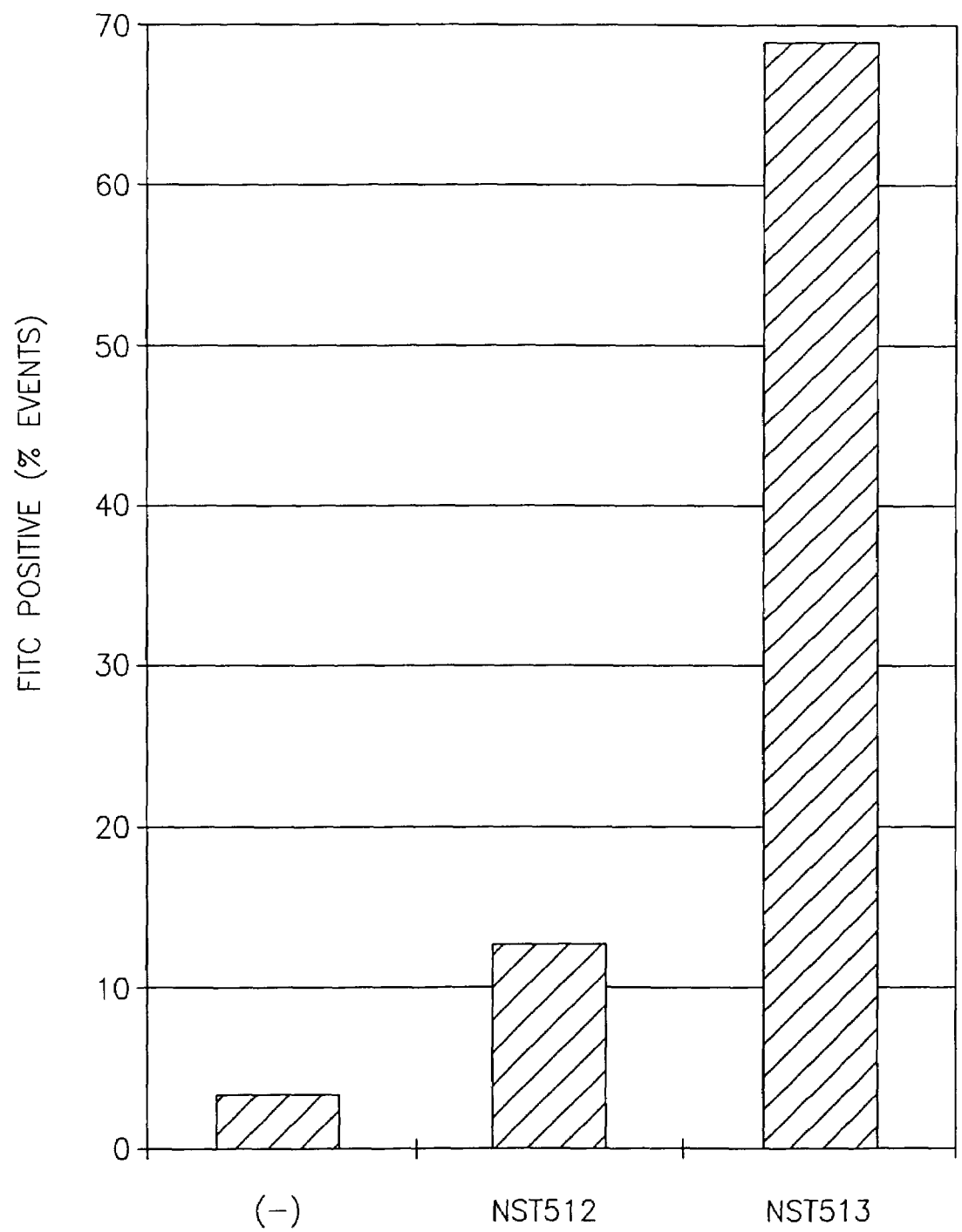
Figure 4A:
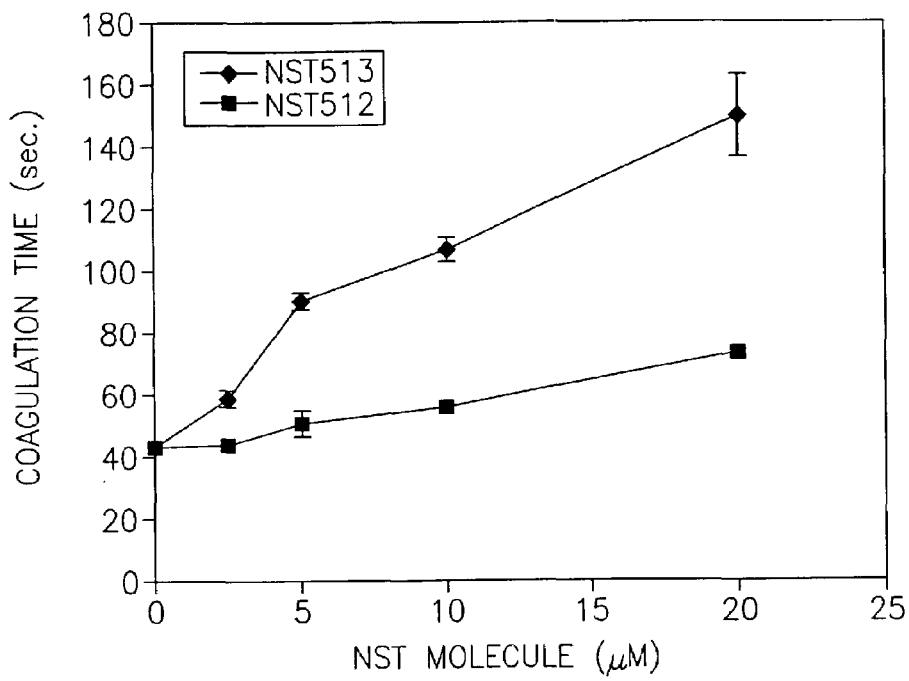
Figure 4B:
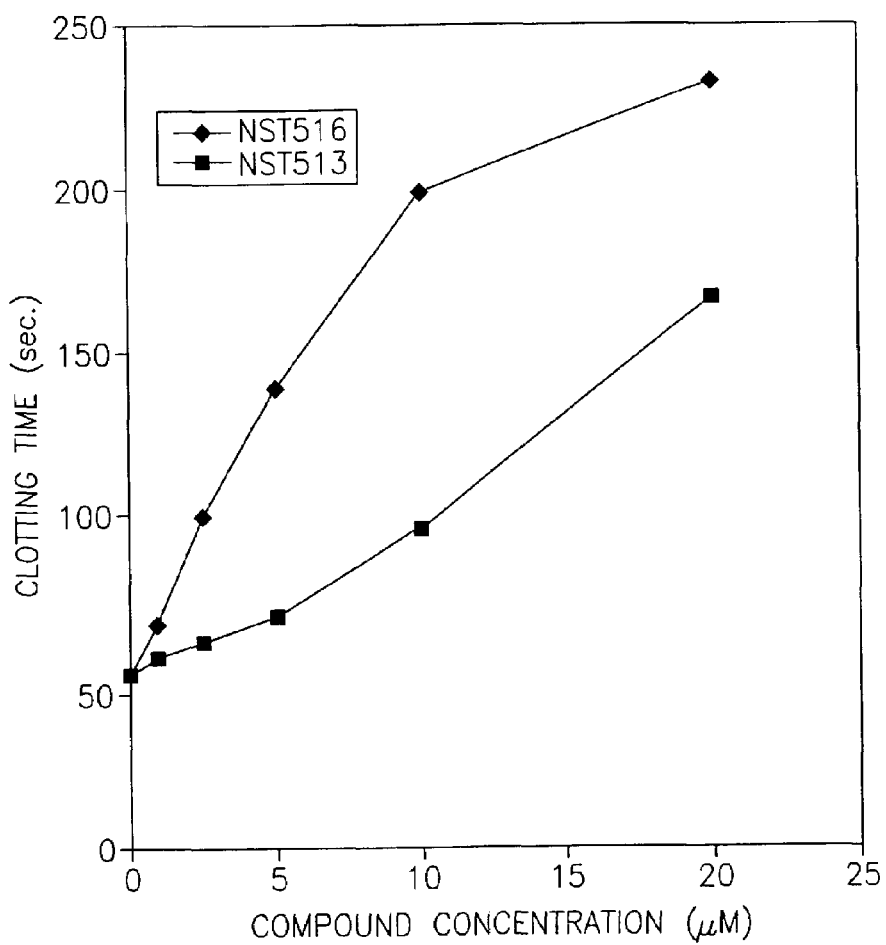
Figure 4C:
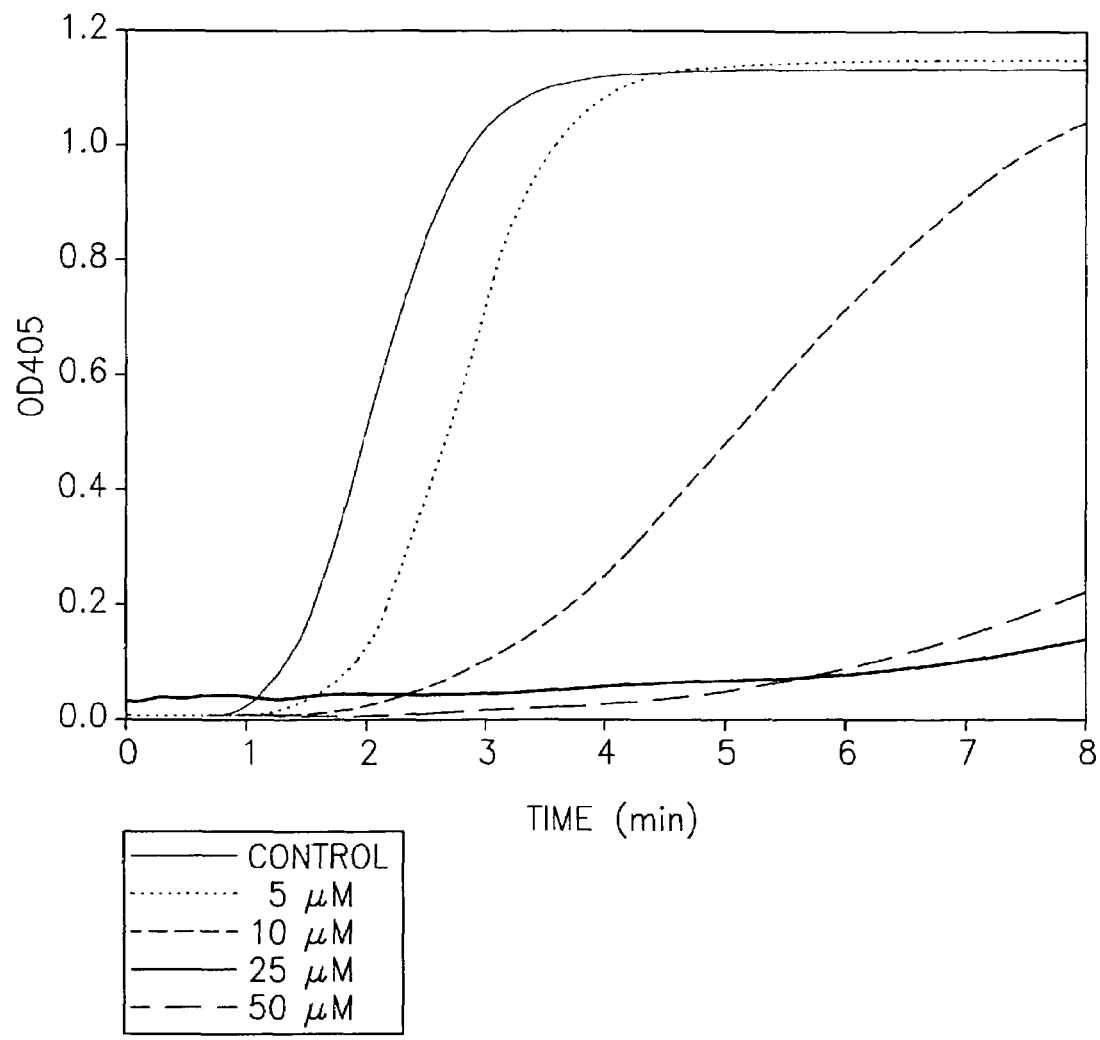
Figure 4D:
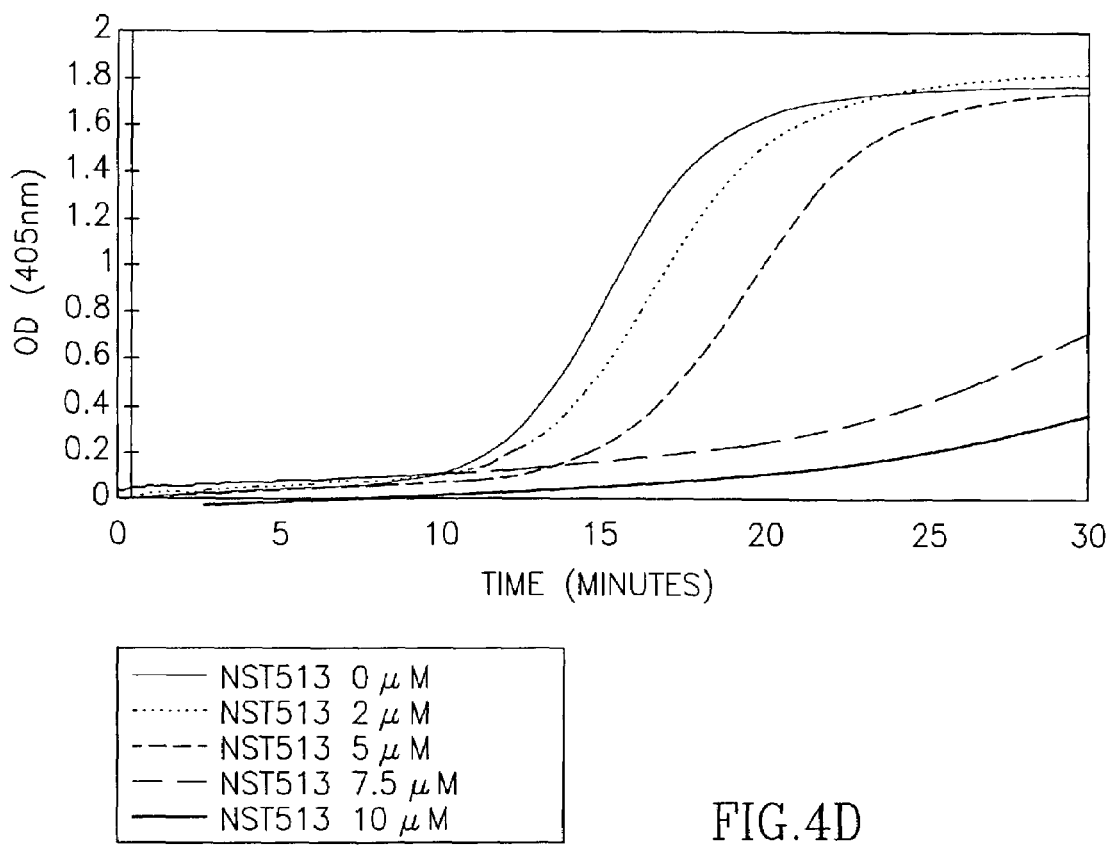
Figure 4E:
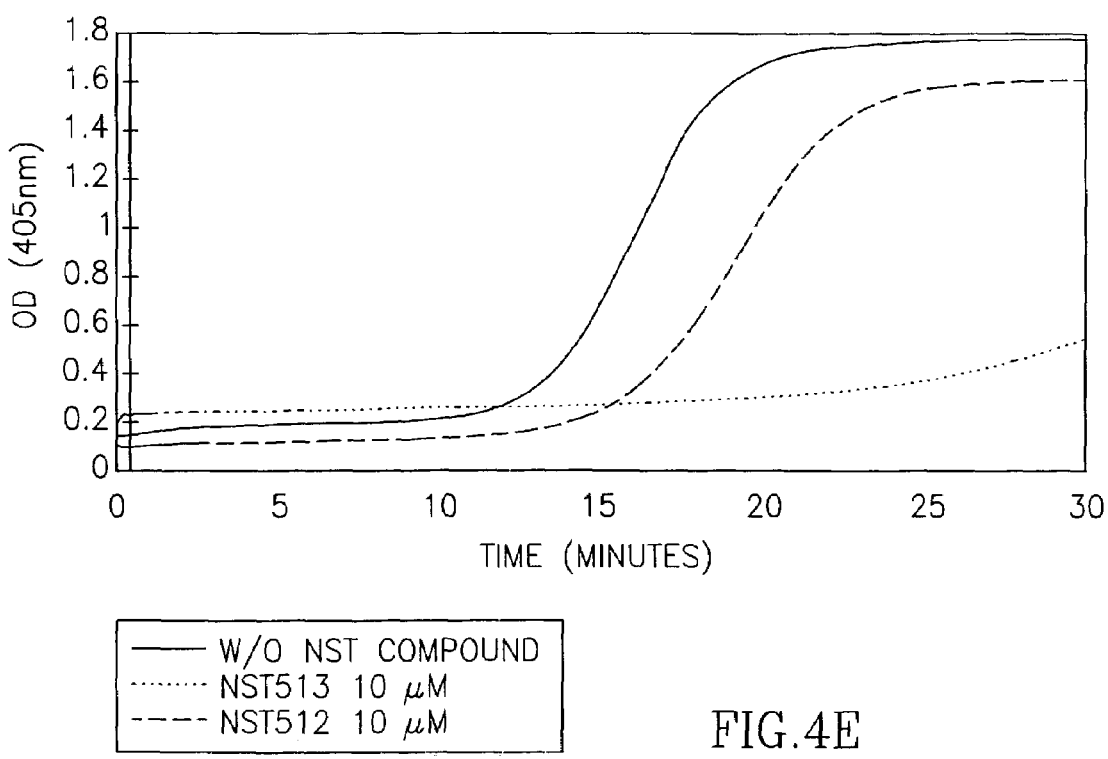
Figure 4F:
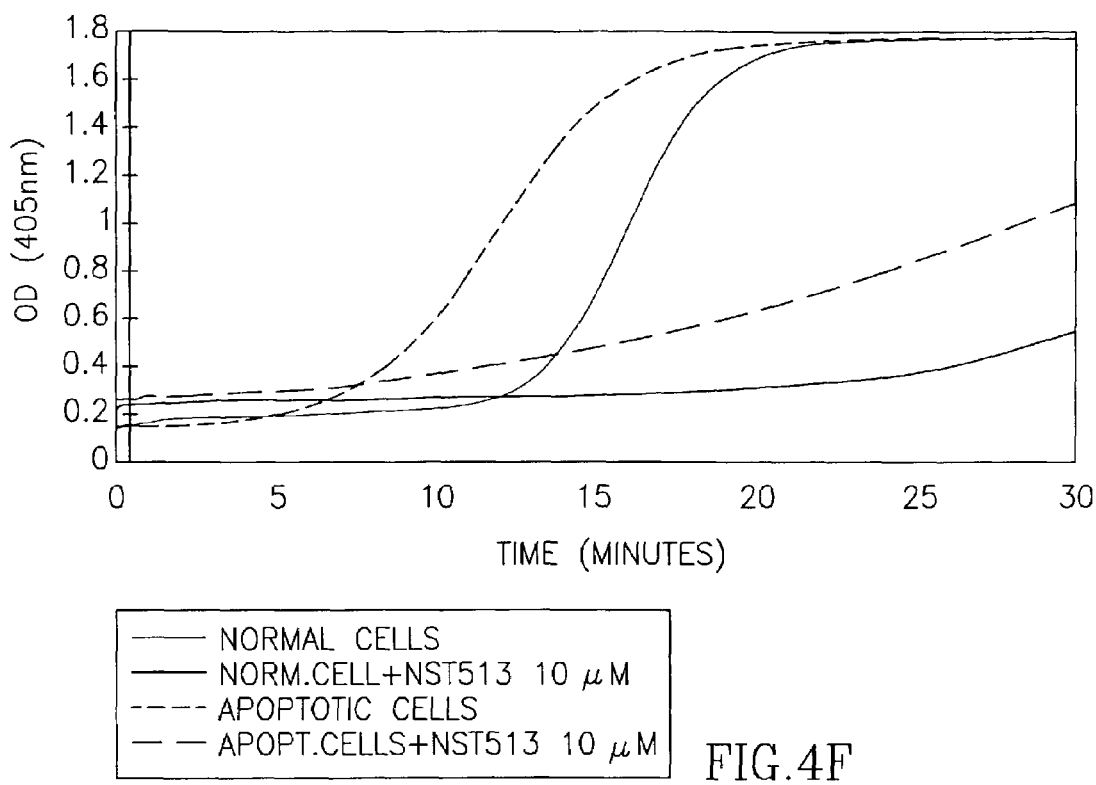
Figure 4G:
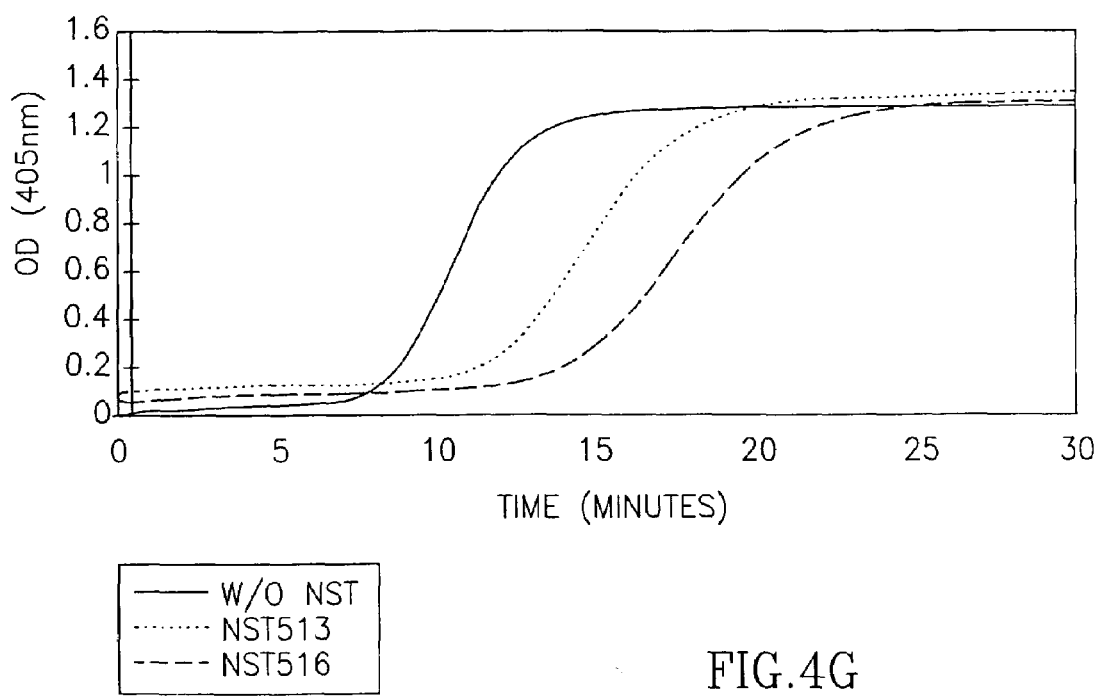
Figure 5A:
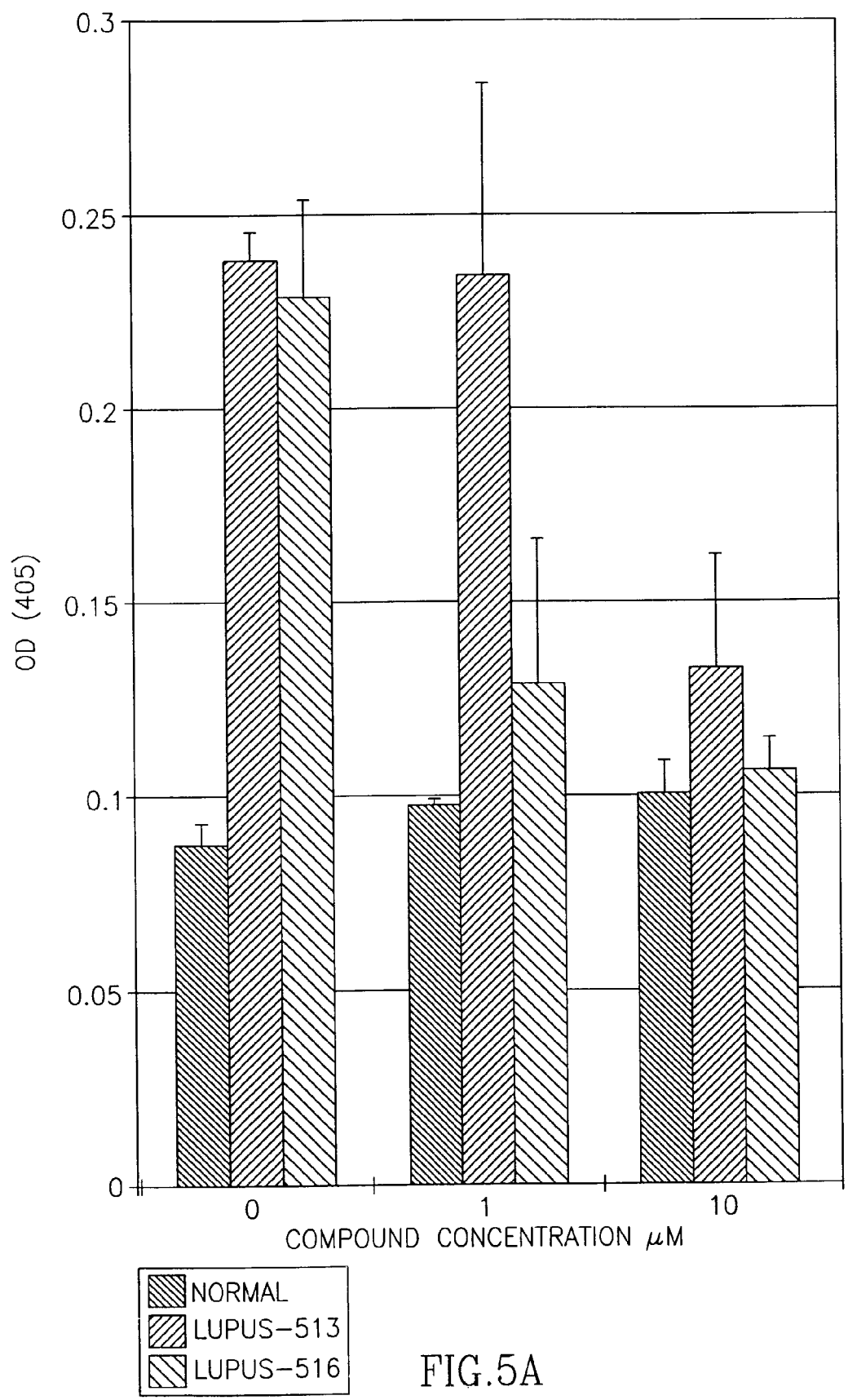
Figure 5B:
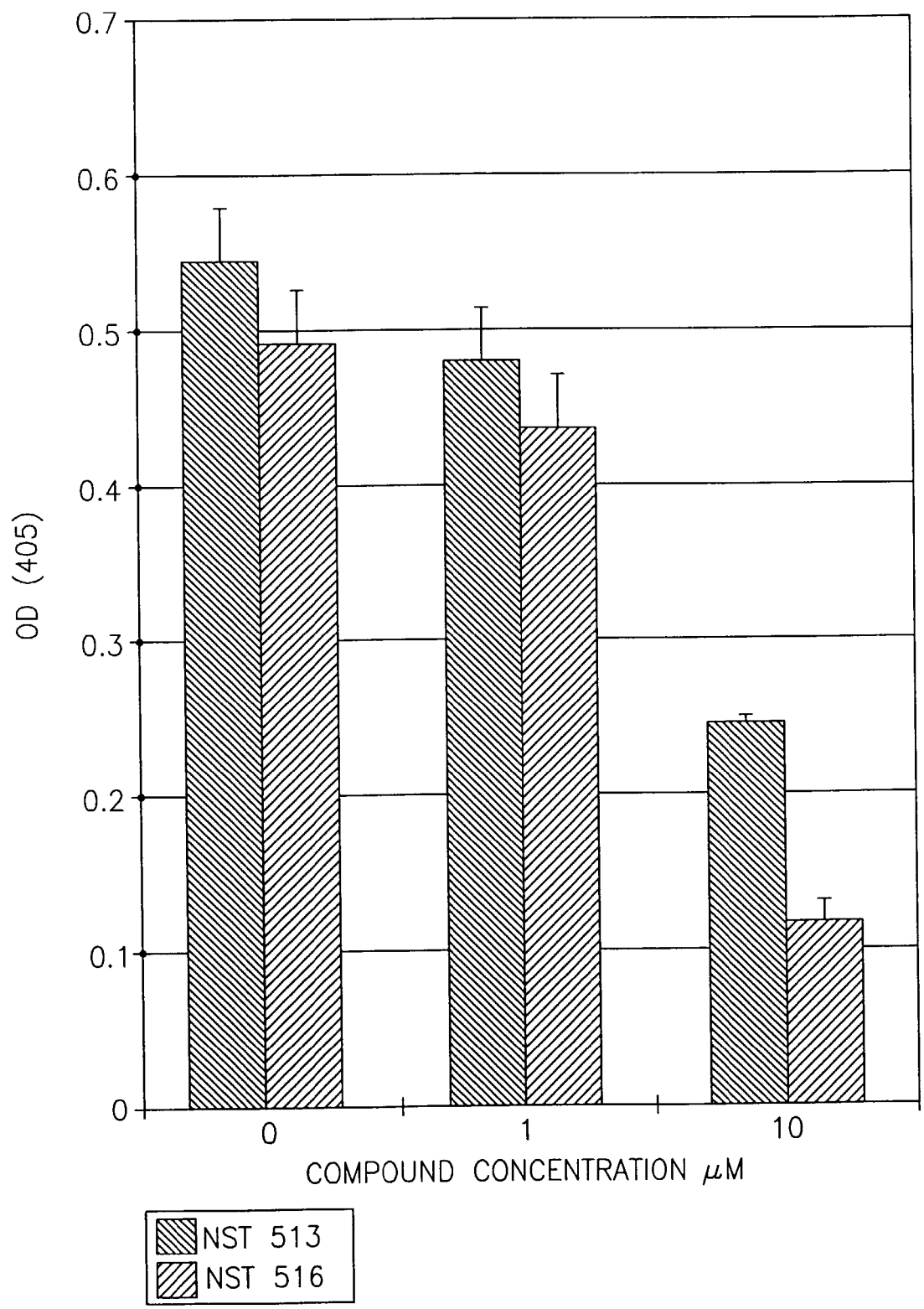
Figure 6:
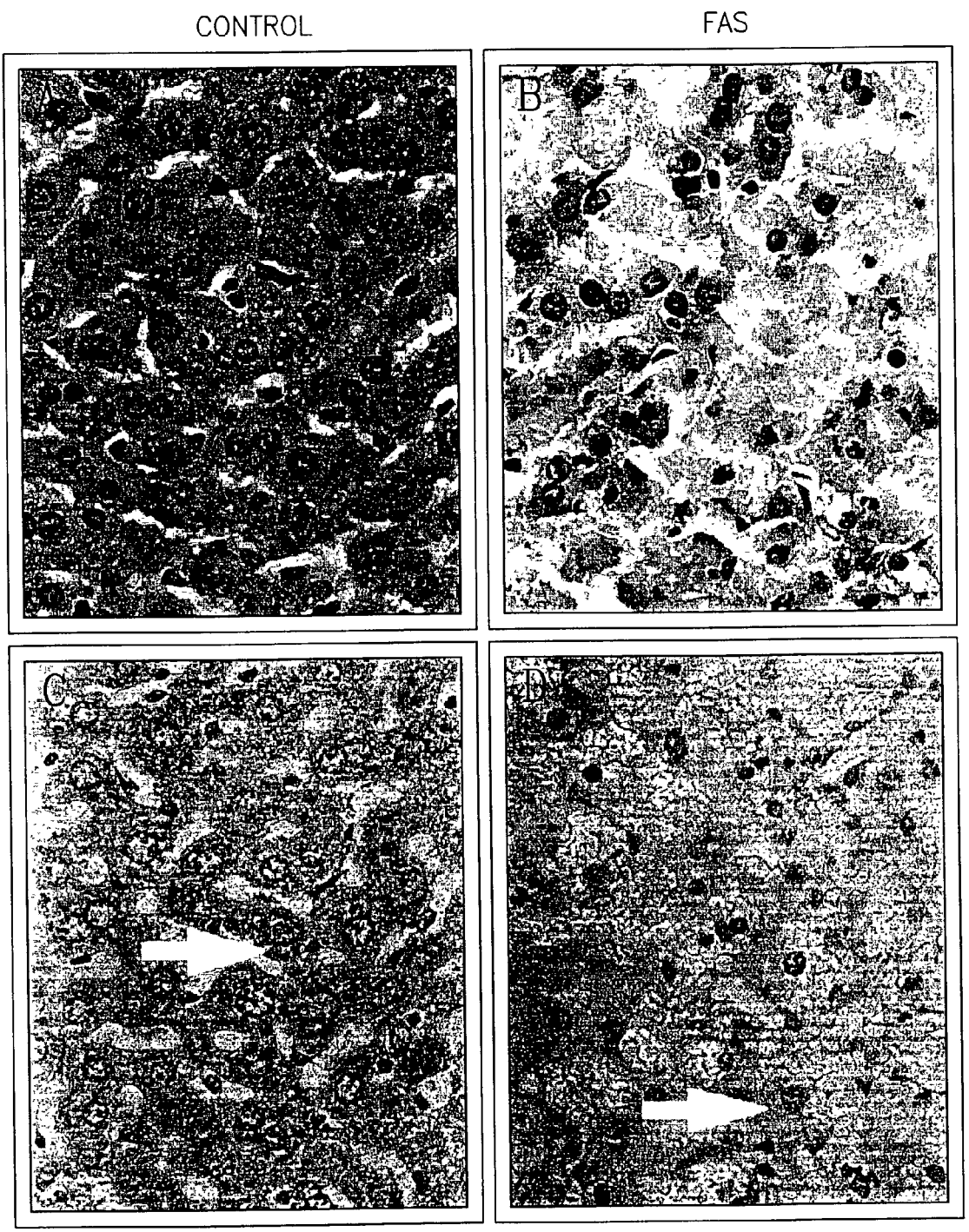
Figure 7:
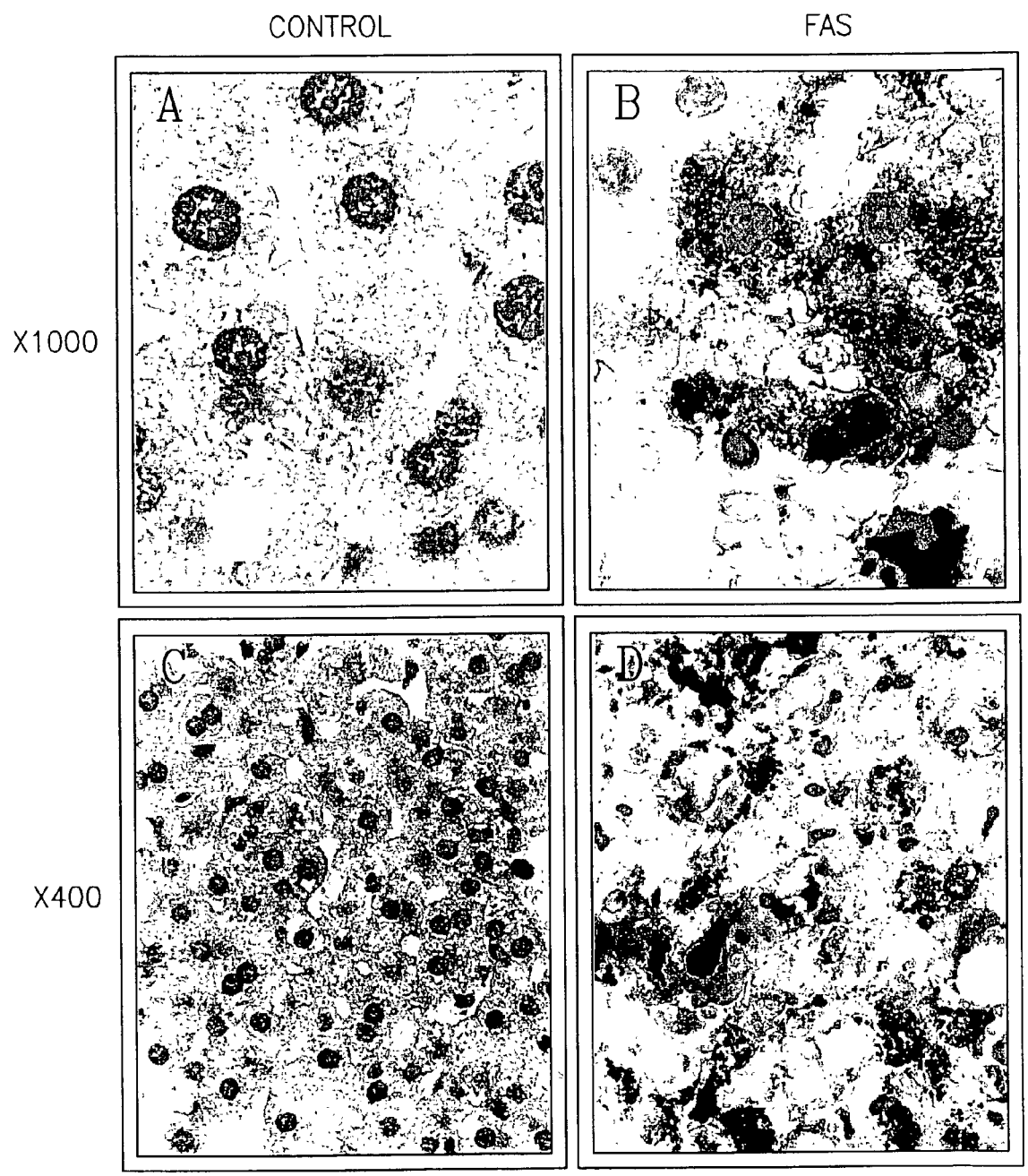
Figure 9:
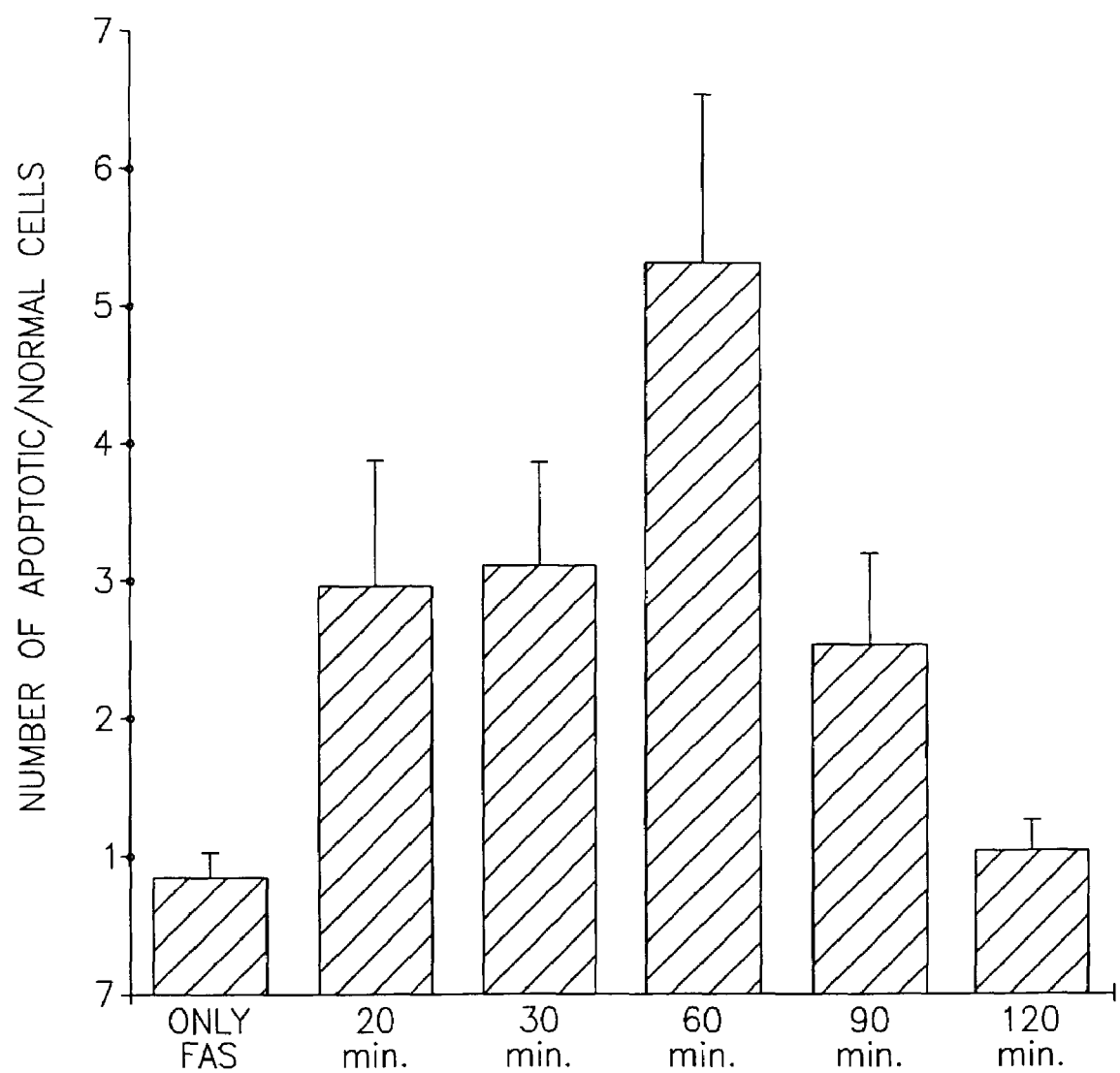

FIG. 1: Structure of NST 500 compound
FIG. 1A: Example of main structural domains of NST500 compounds (General formula I)
FIG. 1B: NST513: detailed structure
FIG. 1C: NST516: detailed structure
FIG. 1D: NST513: computerized model
FIG. 2: Binding of NST513 cyclic compound to single cells presenting anionic phospholipids: Morphological studies
FIG. 2A: Binding of NST513 compound to apoptotic HeLa cells.
FIG. 2B: Binding of NST 513 compound to the trophoblast BeWo cell line
FIG. 3: Binding of NST513 compound to PS presenting cells: Detection by flow cytometric (FACS) analysis.
FIG. 3A: NST513 as a potent marker of apoptotic HeLa cells.
FIG. 3B: NST513 binds to HUVEC cells.
FIG. 3C: NST513 binds to activated platelets
FIG. 3D: NST516 binds to apoptotic Hela Cells.
FIG. 3E: NST516 binds to HUVEC cells.
FIG. 4: Anticoagulant effects of NST500 compound.
FIG. 4A: Anticoagulant effect of NST513: RVV test.
FIG. 4B: NST500 compounds correct the pro-coagulant effect of apoptotic cells: modified APTT test.
FIG. 4C: NST 513 inhibits thrombin generation by apoptotic cells.
FIG. 4D: NST 513 inhibits thrombin generation by endothelial HUVEC cells: Dose-response curve.
FIG. 4E: Inhibition of thrombin generation: effect of compound cyclization on HUVEC cells.
FIG. 4F: Binding of NST513 compound to apoptotic versus normal HUVEC cells.
FIG. 4G: NST516 compound inhibits thrombin generation by endothelial cells.
FIG. 5: NST500 compounds inhibits binding of Lupus derived plasma to anionic phospholipids
FIG. 5A: NST500 compounds inhibit binding of plasma derived from patients with SLE to cardiolipin.
FIG. 5B: NST500 compounds inhibit binding of anti-β2GPI antibodies to HUVEC cells.
FIG. 6: Induction of Fas-mediated apoptosis in the liver.
FIG. 7: NST 513 compound can detect apoptotic cells in vivo.
FIG. 8: Time-course studies (NST513).
FIG. 9: Analysis of pharmacokinetiks studies.

DETAILED EXPLANATION OF THE FIGURES

FIG. 1: Structure of NST500 Compound
FIG. 1A: General structure of compound. See text for detailed description of the composition of each domain. PS=phosphatidylserine, the main anionic phospholipid exposed on cell surface upon CMLA loss.
FIG. 1B: Example of NST513: detailed structure.
FIG. 1C: Example of NST516: detailed structure.
FIG. 1D: Computer assisted model of NST513 compound. Minimum energy structure of NST513 molecule, bonded to biotin and visualized by the Insight II program (from Molecular Simulations Inc. San-Diego, Calif. U.S.A. (MSI)), using an OCTANE workstation (Silicon Graphics Inc, San-Diego, Calif. U.S.A.).
The model was built using the Builder program, and energy minimization was done using the Discover program (MSI), and the Consistent Valence Forcefield (CVFF), according to Dauber-Osguthorpe P. et al., 1988, Proteins Struct. Func. Genet 4, 31–37.
The black residues represent a biotin molecule, and the Myristic acid was drawn in a linear configuration.

Figure 2A:
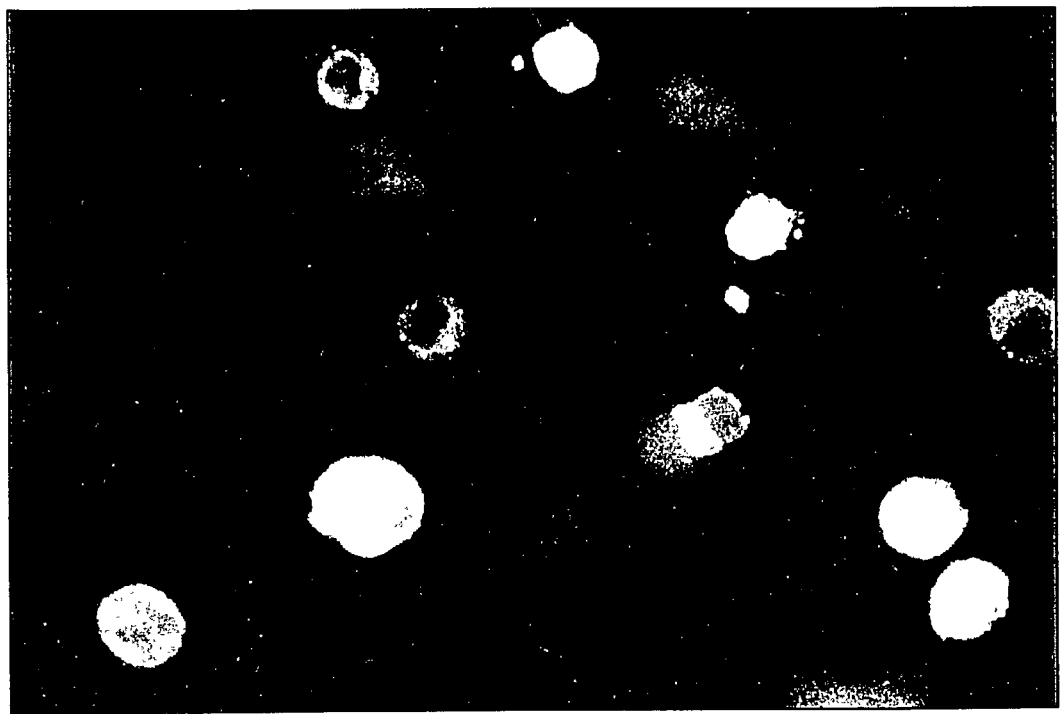
Figure 2B:

FIG. 2: Binding of NST513 Compound to Single Cells Presenting PS: Morphological Studies.
FIG. 2A: Binding of NST513 to apoptotic HeLa cells.
HeLa cells grown on slides were induced to undergo apoptosis by exposure to 500 μM of DA for 18 hours, and then used for immunocytochemistry as described in the text of example 2. Non-treated cells served as control. Cells were stained with 500 nM of the biotinylated NST513 compound and visualized by fluorescent microscopy following the application of sterptavidin reagent labeled with FITC. Typical apoptotic cells are labeled. Magnification is 550.

FIG. 2B: Binding of NST513 to BeWo Cells.
Cells of the placental choriocarcinoma cell line BeWo, were grown on slides for 18 hours, and then stained with NST513 (500 nM).
Detection of binding to cells was as described in the text of example 2. Since trophoblast cells express PS on the outer leaflet of their plasma membrane-labeling by NST513 can be observed. Typical membrane labeling is observed.
Magnification is times 550.

FIG. 3: Binding of NST513 Compound to Phosphoilipid-Presenting Cells: Flow Cytometry Analysis (FACS).
FIG. 3A. NST513 as a potent marker of apoptotic HeLa cells.
HeLa cells were treated with 500 μM of DA for 18 hours. Control and advanced apoptotic cells were collected as described in Example 2. Cells were subjected to 2 different staining protocols:
I. PI and FITC only, with no compound.
II. PI and FITC staining with NST513 compound.
For each of the treatments, the percentage of the double stained cells was determined. The concentration of the compound used was 500 nM. As shown, the cyclic compound NST313 specifically binds to apoptotic cells, as compared to control cells. FIG. 3A1 is a histogram collected from FACS analysis and FIG. 3A2 is quantitative presentation of FIG. 3A1. Values are from a representative experiment.

FIG. 3B. NST513 binds to endothelial (HUVEC) cells.
Endothelial HUVEC cells, are characterized by presentation of anionic phospholipids on their plasma membrane. Cells were incubated with NST512 or NST513 (at a concentration of 500 nM) or buffer alone, and then with streptavidin conjugated to FITC. For each treatment, the percentage of cells that were stained with FITC was determined. Values are from a representative experiment. As shown, the cyclic compound NST513, can serve as a marker for binding to endothelial cells. Binding of the control linear compound, NST512, was residual.

FIG. 3C: Selective binding of NST513 compound to activated platelets.
Activated platelets represent a dramatic case of CMLA loss, resulting in exposure of PS on their plasma membrane, that serves the biological function of assembling coagulation factors on the surface of the activated platelets, thus inducing the coagulation process. The ability of NST513 (at 2 μM) to bind selectively to activated platelets was demonstrated by FACS analysis.
(1) FACS dot plot demonstrating a change in the fluorescenc as a function of platelets activation. The change was induced upon binding to NST513.
(2) Quantitative analysis of the FACS results: In the left panel, a 20 times increase in the FITC mean value is demonstrated, reflecting the higher binding intensity of NST513 to activated platelets. The right panel exemplify that upon activation of platelets, a 6 fold increase in the % of cells stained with NST513 can be obtained. These results demonstrate the ability of NST513 to bind selectively to activated platelets.

Figure 3D:
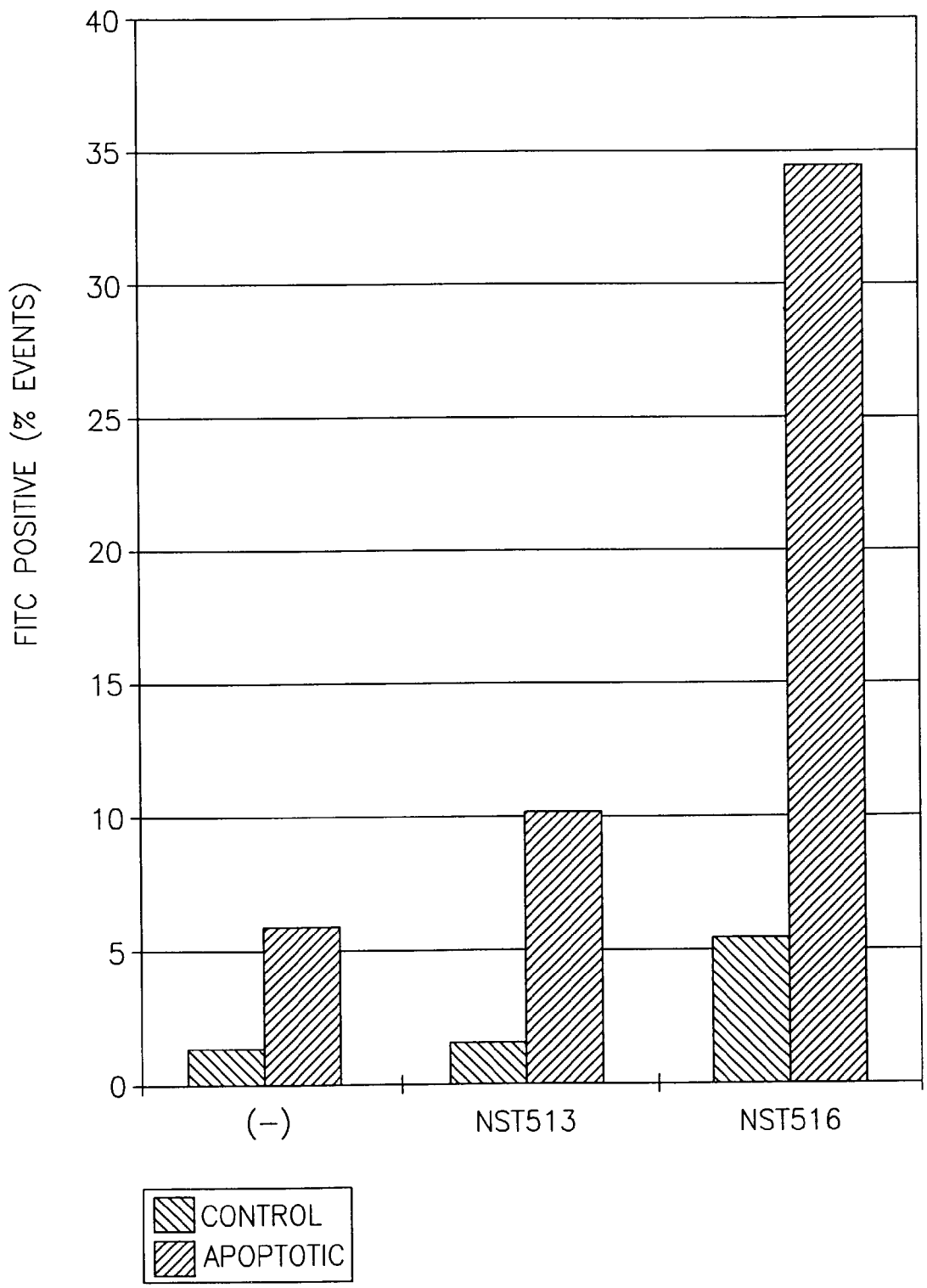
Figure 3E:
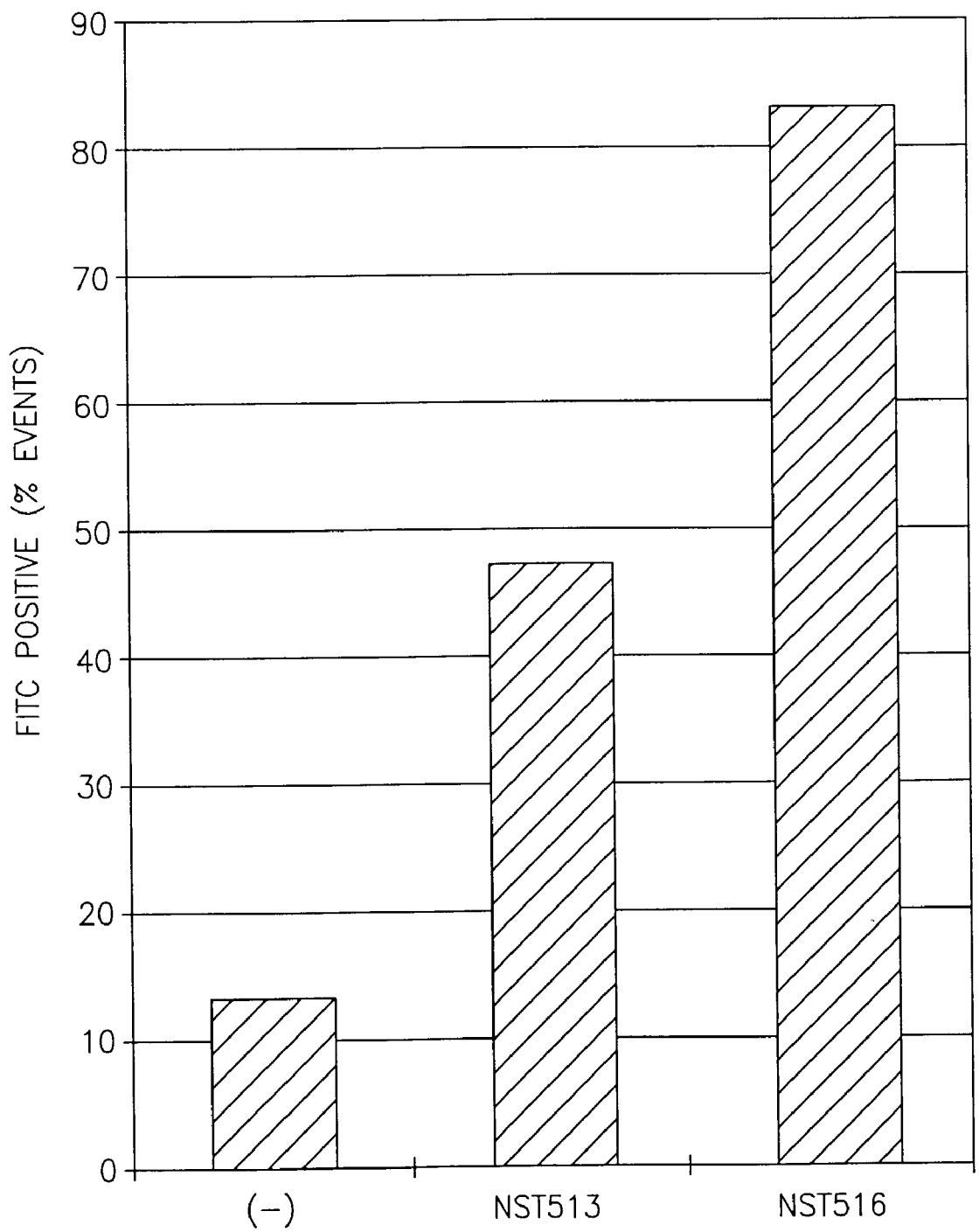

FIG. 3D: NST516 compound binds to apoptotic cells.
Apoptotic Hela cells were prepared as described for FIG. 3a. Binding of NST516 and NST513 at a concentration of 250 μM to apoptotic cells is demonstrated. As shown, at this concentration, the NST516 compound exhibited a 3.5 fold higher binding than NST513 to apoptotic cells. Results are from a representative experiment.

FIG. 3E: NST516 binds to HUVEC cells.
HUVEC cells were used to evaluate the potency of NST516 to bind to PS presenting cells. The experiment was performed as described for FIG. 3B. Compounds were used at a concentration of 250 μM. As shown, NST516 was more potent than NST513 in binding to HUVEC cells, and 70% higher FITC labeled cells were obtained when NST516 was used, as compared to NST513.

FIG. 4: Anticoagulant Effects of NST500 Cyclic Compounds.

FIG. 4A: Anticoagulant effects of NST513: RVV test.
Inhibition of Russell Viper Venom (RVV)-mediated clotting was measured for NST513 compound. Clotting time in the presence of compounds was measured using normal plasma, pre-treated with NST513 compound. Parallel experiments were carried out with the linear compound NST512. The compounds were used at a concentration of 2.5–20 μM. The NST513 compound manifested anti-coagulant effects and prolonged the clotting time by a factor of 3.75, as compared with NST512 that prolonged the clotting by 1.75 times. The graph represents 3 independent experiments.

FIG. 4B: NST500 compounds inhibit the pro-coagulant activity of apoptotic cells.
A modified APTT coagulation test was used to determine the pro-coagulant activity of apoptotic cells. Samples of apoptotic cells were used with or without pre-incubation with NST500 compounds, at concentrations of 2.5–2.2 μM.
Clotting time of apoptotic cells treated with NST516 compound was compared to that of cells treated with NST513 compound. While no change in the clotting time ratio was observed for cells treated with NST512 (not shown), a marked and dose dependent inhibition of clotting time was obtained for cells treated with both NST513 and NST516. However, NST516 exhibited higher potency than NST513 and delayed the clotting time of apoptotic cells by a factor of 4.5, whereas NST513 provided a 3.2 times inhibition.
NST500 compounds not only correct the pro-coagulant activity of apoptotic cells, but also delay the coagulation time further than that of control non-treated cells, which is 80 seconds.

FIG. 4C: NST513 inhibits thrombin generation mediated by apoptotic cells.
A thrombin generation assay was used to demonstrate the pro-coagulant activity of apoptotic cells, as described in example 3. Apoptotic HeLa cells, treated with 500 μM of DA for 18 hours were used with or without pre-incubation with different concentrations (5–50 μM) of NST513.
Inhibition of thrombin generation was observed already in the presence of 5 μM of NST513. The effect of NST513 is dose dependent, and at a concentration of 25 μM, the compound can fully block the ability of pro-coagulant apoptotic cells to induce thrombin generation. The graph demonstrates a representative experiment.

FIG. 4D: NST513 inhibits thrombin generation mediated by HUVEC cells: Dose response.
Measurement of thrombin generation on the surface of endothelial HUVEC cells was carried out in the same manner as described in FIG. 4C for apoptotic cells. NST513 compound, at concentrations of 2–10 μM was used to inhibit thrombin generation. As demonstrated in the graph, 10 μM of NST513 can fully block thrombin generation by HUVEC cell's surfaces. A typical representative experiment is presented.

FIG. 4E: Effect of compound cyclization on HUVEC cells mediated-thrombin generation.
The ability of the cyclic NST513 to inhibit thrombin generation on the surface of HUVEC cells was compared to that of the linear NST512 compound. Experiments were carried out as described above, and the compounds were used at a concentration of 10 μM. A dramatic inhibition of thrombin generation was achieved with NST513, whereas NST512 was much less potent.

FIG. 4F: Effect of NST513 compound on apoptotic versus normal HUVEC cells.
HUVEC cells were induced to undergo apoptosis by treatment with staurosporin. Apoptotic HUVEC cells expose more PS on their plasma membrane, thus serving as a more potent surface for binding of coagulation factors. As a result, the lag time needed for thrombin generation by apoptotic cells is shorter by 5 minutes, compared to normal HUVEC cells. The ability of NST513 to inhibit thrombin generation mediated by the apoptotic cells was compared to that mediated by non-treated cells. At a concentration of 10 μM, both types of cell populations were effected and the thrombin generation was markedly inhibited.

FIG. 4G: NST516 inhibits thrombin generation by endothelial cells. The effect of NST516 compound on thrombin generation mediated by normal HUVEC cells was measured as described for FIG. 4D. NST516 compound was used at a concentration of 5 μM. As compared to NST513, NST516 is more potent in inhibiting thrombin generation.

FIG. 5 NST500 Compounds Inhibit Binding of Plasma Derived from SLE Patients to Anionic Phospholipids.

FIG. 5A: NST500 compounds inhibit binding of plasma derived from SLE patients to cardiolipin.
Cardiolipin (CL) coated ELISA plates were incubated with plasma derived from SLE patients. Detection of binding was performed using an anti human IgG antibody, followed by development with a chromogenic substrate. In the presence of increasing concentrations (1–10 μM) of NST513 and NST516, a marked displacement of IgG derived from SLE patients from the cardiolipin was obtained.

At 1 µM, the NST516 compound exhibited a marked displacement of plasma derived from SLE patients from cardiolipin, whereas the NST513 exhibited similar activity only at 10 µM. Therefore, the compound NST516 was 10 times more potent than NST513 compound in inhibiting binding of plasma derived from SLE patients to CL.

FIG. 5B: NST500 compounds inhibit binding of anti β2GPI antibodies to HUVEC cells.

Competition between NST500 compounds and anti-β2GPI antibodies for binding to HUVEC cells was performed in a modified ELISA assay. Cells were plated in a 96 tissue culture plate. After 18 hours of incubation, the wells were incubated with increasing concentrations of NST500 compounds (1–10 µM) and anti S2GPI antibodies, in the presence of 10% normal plasma as a source of β2GPI protein. The columns represent the relative amount of anti β2 GPI antibodies that bind to the cells.

At a concentration of 10 µM, NST516 exhibited dramatic and significant ability to block binding of anti β2 GPI antibodies to the pro-coagulant surface of cells. NST513 was 50% less potent than NST516. Values are from a representative experiment, and are expressed as optical density (OD) units. Mean±SD of duplicate wells.

FIG. 6: Induction of Fas-mediated apoptosis in the liver

Control non-treated animals were prepared for histological analysis of the liver section and stained with Hematoxylin and Eosin (A) or with TUNEL (C).

Tissues from animals injected with anti-Fas-Ab were prepared as above for Hematoxylin and Eosin (B) or with TUNEL (D).

Two hours after intravenous administration of anti-Fas antibody, typical features of apoptotic events appeared such as advanced chromatin condensation, nuclei crescent shaped, nuclear pyknosis and cell fragmentation (arrow pointing apoptotic hepatocyte). Many red blood cells penetrate the liver and changes were also focally associated with hemorrhage (FIG. 6B) in the entire lobule. Magnification is ×400

FIG. 7: Staining of apoptotic cells with NST513

NST513 staining (brown immunostaining product-in the figure is shown as a dark spot) was observed at cytoplasma and cytoplasmatic border of apoptotic hepatocytes.

(A and C): control non-treated animals, stained with NST500 compound, at a concentration of 5.5 µM.

(B and D): anti-Fas treated animal, stained with NST513 compound as above.

Magnification was ×1000 (for A and B) and ×400 (for C and D).

FIG. 8: Time-course studies (NST513).

The appearance and disappearance of the compound NST513 from the liver following its injection to mice was determined. Sections from animals were treated with anti-Fas and with the NST513 compounds shown herein and were collected at different time intervals after the injection of NST513. The time points shown here are 20, 60, 90, 120 min after injection.

(A): Twenty minutes after the injection of NST513, strong staining could be observed.

(B): Staining of apoptotic cells peaked after 60 minutes from the time of the injection of the NST513 compound. This staining appeared only in mice treated with anti-Fas antibody.

(C–D): Staining of apoptotic cells with the NST513 compound slowly declined, when the liver was sectioned 90 and 120 minutes after NST513 injection.

Two hours after the injection, NST513 compound still exhibited slight staining.

Magnification is ×200.

FIG. 9: Analysis of time-course studies

Appearance and disappearance of the NST513 compound was examined in the following time intervals: 30, 60, 90, 120 min. After injection of the molecule to anti-Fas treated mice. The data presented here correspond to the average ratio between the number of apoptotic versus non-apoptotic cells in a field. For each time interval, 20 fields were counted, at a magnification of ×400. Twenty and thirty min. from the time of injection, a 3.7 higher ratio of apoptotic cells were stained with NST513 as compared to control animals, that were injected with anti-Fas only. Staining appeared to peak after 60 min, in which a 6.5 times higher ratio than the control was obtained. Staining of apoptotic cells slowly declined after 90 min. and at 120 min. the level of staining was similar to the control.

EXAMPLES

Example 1

Synthesis of NST 500 Cyclic Compounds

General Description of the Preparation of N-Terminal Myristoylated, Biotinylated Cyclic Peptide Orthogonally protected diaminoacid was loaded on a solid support. Then the ω-amino protecting group was removed and biotin was introduced to the amino acid resin in the presence of coupling reagent and base, or by using a pre-activation method (e.g. conversion of biotin to its active ester, azide, anhydride). Then, the α-amino protecting group was removed and the peptide was prepared sequentially on the solid support.

Following the removal of the α-amino protecting group of the N-terminal amino acid, myristic acid was introduced to the peptide-resin under conditions which were similar to those used during the coupling of the amino acids. Then, the peptide was cleaved from the solid support, purified and characterized using HPLC/MS.

Method of Cyclization: Cyclization of the peptide via an intramolecular di-sulphide bridge was formed by air oxidation, iodine treatment, removal of S-Acm protecting groups on the Cycteine residues with mercury acetate followed by air oxidation, or simultaneous deprotection/oxidation with Tl (TFA)$_3$. Cyclization was also carried out by an amide bond which was formed either while the peptide was still attached to the resin, or in solution, as follows:

An amine and a carboxyl side chains were protected by Fmoc and Ofm protecting groups or by Allyl and Alloc protecting groups respectively, during the synthesis. While the peptide-resin was attached to the resin, these protecting groups were removed and an amide bond was formed using an appropriate coupling reagent. Then, the peptide was cleaved from the resin, purified, lyophilized and characterized by HPLC/MS.

Branched Multivalent Peptide

A peptide was bound to a Fatty acid-synthetic skeleton and can obtain 2, 4, 8 or 16 peptide sequences on the skeleton (4 valent skeleton indicated in the following formula). In the formula A is an amino di-carboxylic acid.

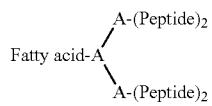

General Preparation of a Tetravalent Peptide:

A fatty acid is coupled to A—(Y)$_2$ where Y is a protecting group of the carboxyl group. Then, the Y protecting group is removed and the Fatty acid-X is coupled with two equivalents of A—(Y)$^-$$_2$. Y is removed and the skeleton is then coupled with a protected peptide prepared on a solid support and purified as described in the general description above, with the following changes: 2-Chlorotrityl resin was used as a solid support and 1% TFA in DCM was used as cleavage conditions. The skeleton-(peptide)$_4$ obtained was purified, lyophilized and characterized by HPLC/MS.

Synthesis of Myristate-KVSFFCKNKEKKCK (SEQ ID NO:1) (Biotin)-OH

Loading of Lys(Mtt) on a Solid Support 2.5 gr Fmoc-Lys(Mtt)-OH was dissolved in 150 ml NMP. 620 mg of HOBt was added following the addition of 1.3 gr of TBTU. Then, 3.5 gr of Rink amide resin (0.58 mmole/gr) was added and the reaction was stirred at room temperature for 3.5 hr. Then, the loaded resin was washed with NMP, MeOH, DCM and then dried in vacuum. 4.4 gr. of loaded resin was obtained.

Preparation of Lys(Biotin)-Resin

Fmox-Lys(mtt)-Resin was stirred with a mixture of 1% TFA, 0.1% TIS in DCM at 0° C. for 30 min and then 1 hr at room temperature. Then, the resin was washed with DCM, NMP and again with DCM. This procedure was repeated two times. This resin was then swelled with 100 ml NMP in the presence of 980 mg Biotin, 1.3 gr. TBTU, 620 mg HOBt and 1.05 ml DIEA. The reaction mixture was stirred for 4 hr. Then, the resin was washed with NMP, DCM, MeOH and dried in vacuum. 4.6 gr. Fmoc-Lys(Biotin)-Resin was obtained.

Synthesis of the Peptide Backbone

Peptide synthesis was accomplished using an ABI 433A peptide synthesizer with HBTU/HOBt coupling reagents. Amino acids used were Fmoc-Nα protected. Trifunctional amino acids were side chain protected as follows: Ser(tBu), Lys(Boc), Asn(Trt), Glu(OtBu). 400 μmol of Preloaded Lys(Biotin)-Resin was placed in the reaction vessel. Each Fmoc amino acid was activated in situ using TBTU/HOBt and subsequently coupled to the resin for 50 min. DIEA was used during coupling as a non nucleophilic base. The Fmoc protecting group on the α amine was then removed with 20% piperidine in NMP for 20 min. 2.5 equivalents of the activated amino acids were employed in the coupling reactions. The deprotection and coupling steps were repeated with the addition of each subsequent amino acid until the peptide synthesis was completed. The final amino acid was deprotected using 20% piperidine in NMP, and coupled with myristic acid under the same conditions as with amino acids introduced. The peptide-resin was washed with NMP, followed by DCM, and dried in vacuum.

Cleavage from the Solid Support

A cleavage mixture consisting of TFA 95% and TIS 5% was added to the peptide-resin (20 ml cleave mixture to 1 gr. resin). The solution was stirred at room temperature for 60 min. The resultant slurry (resin) was filtered using a sintered glass filter. The resin was washed twice with TFA. The filtrate was concentrated to a volume of 1 ml using stream of nitrogen. Following the addition of cold diethyl ether (20 ml) the solution was cooled on ice bath. After 60 min, the peptide was precipitated by centrifugation, washed with cold ether and dried in vacuum. 790 mg of the crude peptide was obtained.

Purification and Characterization of the Linear Peptide 300 mg Peptide was purified by RP-HPLC on C$_{18}$ 5 μm Phenomenex Kromasil column (10 mm I.D.×25 cm). Samples were eluted using the following gradient: A, distilled H$_2$O 0.05% TFA; B. Acetonitrile 0.05% TFA; λ=214 nm; flow 5 ml/min.

The extent of purity for each peptide was monitored by rechromatography on C$_{18}$ 5 μm Phenomenex Kromasil column (4.6 mm I.D.×25 cm) analytical column, flow 1 ml/min. Characterization of the peptides was performed by FAB-MS.

After purification, 66 mg peptide was obtained at >95% purity (non calibrated RP-HPLC, acetonitrile/water 0.1% TFA gradient from 25% to 50% acetonitrile at 30 min. MS(ES) calcd. m/z (MH$^+$/2) 1076.7, found 1077.2.

Cyclization, Purification and Characterization of the Linear Peptide 46 mg purified peptide was dissolved in 200 ml water. the pH was adjusted to 7.5–8.0 with 1 M NH$_4$OH. The reaction mixture was stirred for 2 days, while air was bubbled through the solution. Then the solution was freeze dried and purified under similar conditions as described above. 12.6 mg of peptide was obtained at 85% purity (non calibrated RP-HPLC, acetonitrile/water 0.1% TFA gradient from 25% to 50% acetonitrile at 30 min. MS (ES) calcd. m/z (MH$^+$/2) 1075.7, found 1076.2.

Example 2

NST513 as a Marker for Detection of PS Exposing Cells.

A. Detection of Binding of NST513 Compound to Single Apoptotic Cells, Using Fluorescent Microscopy.

Binding of NST513 molecule to apoptotic HeLa cells was performed according to the following procedure: HeLa S3 cells (ATCC CCL-2.2) were cultured on a glass chamber slide (Nunc, 177402) on a culture area of 0.8 cm$^3$. Chamber slides were pre-coated with 0.1% gelatin (G-1393 Sigma). Cells were seeded at a density of 8×10$^4$ cells/chamber, in a volume of 300 μl of culture medium. Apoptosis was induced by treatment with dopamine (RBI, MA, USA). Following 24 hours of incubation, the medium was replaced by a low serum-containing medium (2% FCS), with 500 μM of dopamine, for 18 hours. Non-treated cells that served as control, were kept in the growing medium without dopamine.

For evaluation of apoptosis, cells were stained with 1 mg/ml of Hoechst 33342 dye (Molecular probes). Twenty minutes later, cells were visualized under UV light microscopy and the relative number of apoptotic cells with condensed or fragmented chromatin was then evaluated and compared with non-apoptotic cells, showing a pale and diffuse staining. Photomicrographs were taken for documentation, but are not shown here.

For staining with NST500 compounds, the tested cultures were grown as specified above and washed twice with TBS (Tris Buffered Saline; 10 mM Tris PH 8.0; 150 mM NaCl). The slides were then incubated with NST513 compound at a concentration of 500 nM for 30 minutes, in a total volume of 100 μl. Slides were then dipped in a Couplin Jar containing 50 ml of TBS, and then incubated with a 1:200 dilution of a sterptavidin reagent labeled with FITC (Jackson Lab.). Incubations were performed for 15 minutes at room temperature, in a final volume of 100 μl. The slides were then washed with TBS as above and were mounted with Fluoroguard antifade reagent (from Biorad Calif., USA).

As a positive control, binding of Annexin V was performed using commercial kit (Genzyme, Mass.). Binding was evaluated with a fluorescent microscope (IX70; Olympus), using an NIBA filter (Narrow Interference Blue A from Olympus) and a ×400 magnification.

The results are shown here in FIG. 2A. Labeled apoptotic cells are indicated. A control non-treated culture of HeLa cells did not exhibit significant labeling by NST513 molecule (not shown). Binding of Annexin V exhibited similar pattern as NST513 compound (not shown). This example indicates that NST513 compound can serve as a potent detector of apoptotic cells and its associated membrane alterations.

B. Detection of Binding of NST513 Compound to Single Trophoblast Cells.

The Human choriocarcinoma cell line BeWo that express low levels of PS on its plasma membrane (Rote N S et al., 1995, American J. of Reproductive Immunology 33, 114–121), was obtained from ECACC, cat # 86082803 and maintained in Ham's F12+ medium (01095-1A, Bet-Haemek, Israel). The medium was supplemented with 2mM of L-Glutamine; 100 units/ml of penicillin; 100 μg/ml of streptomycin, and 10% fetal calf serum (Bet-Haemek). The cells were passaged using 0.05% trypsine/EDTA (03-054-1B, Bet-Haemek,). For binding experiments, cells were grown on slides for 18 hours, and incubated with NST513 compound at a concentration of 500 nM. Processing of the sample was as described for HeLa cells and is shown in FIG. 2B. Binding of the compound to the whole population of BeWo cells was demonstrated. Staining of a parallel culture with annexin V kit (from Genezyme Mass., USA), served as control, and similar staining profile was obtained (not shown).

C. Detection of Binding of NST513 Compound to PS-Exposing Cells by FACS Analysis Detection of binding to apoptotic HeLa cells was performed according to the following procedure: Cells were plated on tissue culture plates at a density of 5×10$^6$ cells/10 cm dish, and grown in their normal medium at 37° C. for 18 hr. The medium was replaced with a medium containing 2% FCS and 500 μM of dopamine. Eighteen hours later, floating cells that were identified as advanced apoptotic cells were collected and transferred to a 50 ml tube. To evaluate the level of apoptosis in the cultures, aliquots of 10$^5$ cells from the cultures were plated on 48 wells plate and stained with Hoechst 33342 dye (Molecular Probes) at a concentration of 1 mg/ml for 20 min (as described above). Non-treated cells served as control. For collecting the non-treated cells, the medium of the culture was aspirated and discarded, the cells were rinsed with growing medium and 2 ml of medium were added to the culture dish. The cells were detached from the culture dish using a cell scraper and separated to single cells by passage through a syringe with a 18G needle.

For FACS analysis, cells were incubated with 500 nM of NST513 compound in a final volume of 100 μl TBS containing 5 μg/ml of propidium iodide (PI, P-4170 sigma). The reactions were incubated at room temperature for 40 minutes and then 400 μl of TBS was added and cells were collected by centrifugation at 3000×g for 3 minutes. Cells were washed in 1 ml of TBS and centrifuged as before and detecting of the bound compound was performed using 100 μl of TBS containing streptavidin conjugated to fluorescein (FITC) (016-090-084 from Jackson ImmunoResearch lab. Inc.). Incubation was for 15 minutes at room temperature in the dark. Thereafter, 400 μl of TBS was added and cells were centrifuged and washed again with 1 ml of TBS as before, re-suspended in 400 μl of TBS and then taken for FACS analysis. The FACS analysis was performed on Beckton-Dickinson cell sorter, using lysis II software. Excitation was at 488 nm and emission for FITC detection was at 535 nm and for PI detection at 585 nm.

FIG. 3A demonstrates binding of the NST513 compound to both control and apoptotic cells. Staining with NST513 molecule revealed a strong labeling of apoptotic versus control cells as can be seen by the shift of the dot plot in FIG. 3A panel 1 from low to higher FITC valves. FIG. 3A panel 2 shows quantitation of the signal indicated that a 5.5 fold increase was obtained in the precentage of apoptotic cells labeled with NST513, as compared to non-apoptotic cells. These results indicated that a NST513 compound can specifically bind to apoptotic cells and can serve as a detector of exposure of PS.

D. Detection of Binding of NST513 to Endothelial Huvec Cells by FACS Analysis.

Human Umbilical Vein Endothelial Cells (HUVEC) normally express anionic phospholipids on their outer membrane (Van Heerde W L et al., 1994, Biochem J. 302, 305–312), therefore they can serve as a physiological surface for binding of ligands with an affinity to PS and as a target for binding of NST513 compound. Binding detection was done using flow cytometric analysis to populations of HUVEC cells.

Preparation of Cells for FACS Analysis:

HUVEC (CC-2517, obtained from Clonetics, Walkersville, Md.) were grown on tissue culture flasks in Endothelial cell medium (EGM-2 Bulletkit, CC 3162, Clonetics). Mid-confluent cultures were harvested using Trypsine/EDTA solution (CC-5012, Clonetics). The cells were rinsed twice with TBS containing 2% BSA and kept on ice. Samples of 10$^6$ cells were tested for binding. The incubation with NST500 compounds was performed at a concentration of 500 nm in a final volume of 100 ml TBS+2% BSA containing 500 ng of NST513 or NST512 or no compound.

The reactions were incubated at room temperature for 40 minutes and then 400 μl of TBS-BSA were added and cells were collected by centrifugation at 3000×g for 3 minutes. Cells were washed in 1 ml of TBS-BSA and centrifuged as before and then suspended in 100 μl of TBS-BSA containing streptavidin conjugated to fluorescein (FITC) for detection of the bound biotinylated compound. Incubation was for 15 minutes at room temperature in the dark. Thereafter, 400 μl of TBS-BSA were added and cells were entrifuged and re-suspended in 400 μl of TBS and taken for FACS analysis.

Marked FITC levels were obtained upon binding of NST513 to cells, indicating strong binding of the cyclic molecule to PS presenting cells (FIG. 3B). About 70% of the cells incubated with NST513 were FITC positive while only 12% of the cells incubated with NST512 compound were FITC positive. These data indicated, that although NST512 and NST513 compounds have the same amino acid sequence, the cyclization of NST513 compound dramatically increased the binding to HUVEC.

E. NST513 Selectively Binds to Activated Platelets

Exposure of PS on the outer leaflet of platelets upon their activation is essential for efficient activation of coagulation factors. The ability of NST513 to bind to activated platelets was therefore determined, using FACS analysis. Fresh platelets were received from the Blood Bank in Beilinson Hospital, Israel. The platelets were centrifuged (10 minutes, 2700×g), washed and re-suspended in platelets buffer (137 mM NaCl, 2 mM $MgCl_2$, 0.5 mM NaPi, 5 mM glucose and 20 mM Hepes pH 7.4). 100 µl of platelets were diluted 10 fold and activated for 10 minutes with 2 µM of the calcium ionophore A23187 in the presence of 5 mM of $CaCl_2$. Activated and control non-treated platelets were incubated with 2 µM of biotinylated NST513 for 15 minutes at room temperature. The platelets were then washed with platelets buffer and incubated with 5 µg/ml of streptavidin conjugated to fluorescein (FITC). Incubation was for 15 minutes at room temperature, followed by a wash and suspension in platelets buffer. The labeled platelets were subjected to a FACS analysis as described above. As seen in FIG. 3C (1), the control platelets were stained with low levels of fluorescence. However, upon their activation with the calcium ionophore, the peak of FITC labeled platelets has moved to higher fluorescence values, indicating stronger binding of NST513 molecule. Quantitative analysis of these changes indicated a 6 fold increase in the percentage of platelets stained with FITC as a function of its activation (FIG. 3C (2), right panel) Binding intensity (expressed as FITC mean value in FIG. 3C (2), left panel) of the activated platelets was 20 times higher than that of the control non-treated platelets. The ability of NST513 to selectively bind activated platelets further exemplified its strong affinity to cells which present PS and distinguished a potential role for NST513 as a PS-neutralizing agent that can neutralize the pro-coagulant surface of activated platelets.

F. Binding of NST516 Compound to PS Presenting Cells

The NST516 and NST513 are both analogous compounds of the NST500 series compound. Therefore, their relative performance in binding to PS presenting cells was evaluated in comparison to NST513. Experiments were performed as described earlier, and FACS analysis was used. FIG. 3D demonstrates that at a concentration of 250 µM there is an advantage for using NST516 rather than NST513, since its ability to bind to apoptotic HeLa cells is 3.5 times higher. The relative advantage of the NST516 was exemplified also in binding to HUVEC cells, and is exhibited in FIG. 3E. While NST513 labeled a fraction of about 50% of the HUVEC cells, NST516 was capable of labeling 83% of the HUVEC cells, indicating an 8-fold increase as compared to the background of control cells (without the NST compound). These results indicate a better potency of NST516 as compared to NST513 in binding to PS-presenting cells.

Example 3

Anticoagulant Effects of NST513 Cyclic Compound.

A. Anticoagulant Activity of NST513: RVV Test

Anticoagulant properties of NST513 were exemplified using the standard RVV coagulation assay, as described hereinafter: The RVV reagent LA screen (LACD from Gradipore, Australia), containing RVV and low concentrations of phospholipids was used. Reactions were started by mixing 100 µl of RVV reagent, and 100 µl of quality control plasma collected from normal individuals (84670-11, Instrumentation Laboratory, Italy). Clotting time was detected by visual inspection following mixing the reaction ingredients in a test tube, until the suspension could no longer be aspirated with a pasteur pipette. Clotting time was measured by two separate researchers.

Inhibition of clotting time was measured following addition of NST513 or NST512 compounds (at different concentrations) to the above reaction mixture. 10 µl of NST513 compound was added to 100 ul of normal plasma and incubated for 1 min in 37° C. bath. 100 µl of LA screen was then added and clotting time was detected as described.

Clotting time in the presence of 2.5–20 µM of NST513 or NST512 compound was measured. FIG. 4A demonstrates a concentration dependent effect for each one of the compounds tested. The control clotting time, when no compound was added to normal plasma was 40 seconds. However, In the presence of NST513 molecule, a significant increase (by a factor of 3.5) in the clotting time was observed, whereas the linear compound NST512, was less potent and exhibited a moderate change (by a factor of 1.75, and only at a higher concentration of 20 µM). The $EC_{50}$ (effective dose of 50%) for NST513 compound was 3–5 µM. These experiments demonstrate the anticoagulant potency of NST513 molecule.

B. NST500 Molecules Correct the Pro-Coagulant Activity of Apoptotic Cells.

In a modified APTT test, using apoptotic HeLa cells as a pro-coagulant surface, the potency of NST516 was compared to that of NST513.

Apoptotic and control HeLa cells were prepared as described for the FACS analysis. Equal numbers of apoptotic or control non-treated cells ($5 \times 10^4$) in a volume of 1001, were mixed with 100 µl of normal plasma, incubated for 1 min at 37° C. in a bath and then calcified by addition of 100 µl of 25 mM $CaCl_2$, and clotting time was measured. Inhibition of the pro-coagulant activity of the apoptotic cells by NST500 compounds was tested following pre-incubation of apoptotic cells for 20 min. at room temperature with increased concentrations of the different NST 500 compounds.

The results can be seen in FIG. 4B. A dose-dependent effect was observed for both NST513 and NST516. Clotting time of apoptotic cells was 50 seconds. The addition of NST513 increased the clotting time to 160 seconds, which is an increase by a factor of 3.2, prolonging it far beyond the clotting time exhibited by control non-treated cells. (which is 80 seconds). The addition of NST516 further delayed the clotting time to 225 seconds, indicating an increase of 4.5 times. These results demonstrate the potential use of NST500 molecules as inhibitors of the pro-coagulant properties of apoptotic cells.

C. NST513 Compound Inhibits Thrombin Generation by Apoptotic Cells.

One of the final steps of both intrinsic and extrinsic path-ways of coagulation, is the generation of thrombin from prothrombin. Thrombin is the final protease generated in the sequence of coagulation reaction, and its activity entails conversion of fibrinogen to fibrin, thus forming the clot. Generation of thrombin on the pro-coagulant surface of apoptotic cells was assayed (according to Bombeli T. et al., 1997, Blood 89(7), 2429–2442), by determining its activity, using the chromogenic substrate S-2366 (from Chromogenix, Sweden). Samples of pro-coagulant cells (HeLa cells treated with 500 µM of DA for 18 hours) were used for the assay. Reaction mixture, in a plastic 1 ml cuvette, contained 100 µl of cells ($1.5 \times 10^5$), 350 µl of HBS (150 mM NaCl, 10 mM Hepes pH 7), and 150 µl of normal control plasma, that was re-calcified with 300 µl of 25 mM $CaCl_2$. The reaction was started by addition of the substrate S-2366 to a final concentration of 0.2 mM, and the kinetics of thrombin activity was determined by optical density at $OD_{405}$. Data was collected and analyzed by the Swift kinetics software (Pharmacia). As shown in FIG. 4C, thrombin activity of apoptotic cells can be detected between 1–2 minutes of addition of the chromogenic substrate, and the activity peaked after 3 minutes. 50% of the activity was achieved after 2 min. of substrate administration. To assess whether the anticoagulant properties of NST513 molecule can interfere with thrombin generation on the surface of apoptotic cells, the NST513 compound (at concentrations of 5–50 μM) was pre-incubated with the apoptotic cells, before the addition of the plasma and the reaction substrate. As seen in FIG. 4C, thrombin activity (reflecting thrombin generation) was effectively inhibited in the presence of increasing concentrations of NST513.

The compound NST513 had no direct inhibitory effect on thrombin activity assayed in vitro by addition of compound to commercially available thrombin and the chromogenic substrate as above; (not shown). Therefore, the effect of NST513 on thrombin activity reflects the interference of the compound with thrombin generation, which is driven by binding of the coagulation complex to PS on the cell surface.

At a concentration of 5 μM, there was a delay in the lag time needed for thrombin generation, that reflected the time needed for assembly of the coagulation complex. However, at a concentration of 10 μM, the rate of thrombin generation was also inhibited, therefore suggesting that NST513 inhibited also the number of thrombin complexes formed. Total blockage of thrombin generation was evident at concentrations of 25–50μM of NST513. Concentrations of 5 and 10 μM reduced the time needed for obtaining 50% of thrombin activity by a factor of 1.5 and 2.6, respectively.

D. NST513 Compound Inhibits Thrombin Generation by Huvec Cells

In vivo, vascular endothelial cells are known to catalyze the formation of thrombin, due to expression of PS on their plasma membrane, at which pro-coagulant complexes are assembled (Van Hardee W L et al., 1994, Biochem J. 302, 305–312). Endothelial cells (EC) play an active role in determining the pro-coagulant/anti-coagulant balance in the vascular system (Gimborne M A et al., 1995, Ann. N. Y. Acad Sci 748, 122–132). Perturbed endothelial cells dramatically increase their pro-coagulant state. Therefore, inhibition of thrombin formation on HUVEC cell's surface by NST513 compound was determined. (FIG. 4D). When HUVEC cells ($1.5 \times 10^5$) were incubated with the S-2366 substrate, thrombin generation was evident after a lag time of 12.5 minutes, which reflects the time required to assemble a functional complex on the HUVEC surface. Upon pre-incubation of cells with NST513, a dose dependent inhibition of thrombin generation was detected. At a concentration of 2 μM, there was a slight inhibition of thrombin generation. At concentrations of 5 μM, addition of NST513 molecule further delayed the lag period required to assemble the complex (FIG. 4D). However, in the presence of 7.5 and 10 μM of NST513, a total blockage of thrombin formation was observed over a period of 30 minutes, indicating that the compound competes with the coagulation factors for binding to active sites on the cell's surface (FIG. 4D). When the linear compound NST512 was used at a concentration of 10 μM in the same experimental system, only a slight delay of thrombin generation was obtained, emphasizing the potency of the cyclic NST513 compound (FIG. 4E).

Although endothelial cells represent a partial and natural condition of CMLA loss, several EC-mediated mechanisms exist, that provide them with anti-coagulant properties (Bombeli T at al., 1997, Blood, 89, 2429–2442). Nevertheless, EC can rapidly shift the hemostatic balance and become pro-coagulant. One of the perturbing conditions that drive EC towards the pro-thrombotic state is the induction of apoptosis (Bombeli T at al., 1997, Blood, 89, 2429–2442). Therefore, we tested whether the NST513 compound is able of inhibiting thrombin generation, mediated by apoptotic HUVEC cells. Apoptosis was induced by treatment with staurosporin (STS, a non specific protein kinase inhibitor), that can induce apoptosis in HUVEC cells (Bombeli T at al., 1997, Blood, 89, 2429–2442). Samples of $1.5 \times 10^5$ of HUVEC were treated with STS at a concentration of 50 nM for 16 hours and then were collected as before and used for the thrombin generation assay, in comparison to non-treated HUVEC. As can be seen in FIG. 4F, Induction of apoptosis resulted in a decrease of the lag time needed for assembling of the thrombin generation complex from 12.5 minutes (in non-treated HUVEC) to 7.5 minutes. This enhancement reflects the exposure of additional anionic phospholipids binding sites on the surface of HUVEC, as a function of the apoptotic signal. Concomitantly, co-treatment of apoptoptic HUVEC with 10 μM of NST513 caused marked and substantial elongation of thrombin generation time. The effect of NST513 on apoptotic cells was slightly lower than that on non-treated cells, indicating that in order to neutralize the additional PS binding sites on apoptotic cells, a higher concentrations of NST513 may be required. This evidence further exemplify the linkage between the load of anionic phospholipids exposed on the surface of cells, and the concentration of the blocking NST513 compound that can target it. Similarly, the concentration needed to achieve complete inhibition of HUVEC-mediated thrombin generation was lower than that needed for total blockage mediated by apoptotic HeLa cells (FIG. 4F as compared to FIG. 4C). A possible explanation for that is the lower concentration of PS exposed on normal HUVEC cells as compared to the load of PS exposed on HeLa cell surface upon induction of apoptosis.

The effect of NST516 compound on HUVEC mediated-thrombin generation was studied. Similarly to NST513, a dose dependence inhibition of thrombin generation was detected (not shown). At a concentration of 5 μM, NST516 exhibited a 5 min. delay in thrombin generation, whereas NST513 exhibited a delay of 2.5 min (FIG. 4G). These results indicate that NST516 is a more potent compound in inhibiting thrombin generation on HUVEC cell's surface.

These data exemplified the potency of NST500 compounds as efficient and potent inhibitors of the final step of thrombin generation mediated by PS presenting cells. Furthermore, the ability of NST500 to bind to endothelial cells and inhibit thrombin generation suggests these molecules as candidate agents for promoting the thrombo-resistance state of endothelial cells.

Example 4

A. NST513 Compound as a Competitive Inhibitor of Plasma Derived from SLE Patients for Binding to PS Exposing Surfaces.

The antiphospholipid antibody syndrom (APS) is a thrombophilic condition, characterized by a panel of antibodies that recognize anionic phospholipid-protein cofactor complexes. The antiphospholipid antibodies lupus anticoagulant and anticardiolipin, (present in high concentrations in SLE patients), are associated with several medical disorders including artherial and venous thrombosis, and recurrent pregnancy loss (Rand J H et al., 1998, Blood. 92, 1652–1660). Since the NST500 compounds are capable of binding to anionic phospholipids, their ability to compete with plasma derived from SLE patients for binding to anionic phospholipid presenting surfaces was tested. Noncellular negatively charged phospholipid coated surface (cardiolipin) were chosen as a target for binding.

Cardiolipin (CL), a negatively charged phospholipid, was used to demonstrate binding of plasma derived from SLE patients to anionic phospholipids in ELISA assays that were performed according to Hazeltine et al., 1988. CL, (Diphosphatidylglycerol, c-1649, Sigma), prepared at 50 μg/ml in ethanol, was added to a 96 well plate (100 μl/well) using Immunolon 4 plates (Dynatech, Chantilly, Va.) and incubated for 16–20 hr for evaporation of ethanol. As control, wells were coated with ethanol only. The coated plates were washed 3 times with 100 μl of blocking buffer (PBS containing 0.3% gelatin (Sigma) and 1 mM EDTA) to block non specific binding. A 5 min incubation time was used between each wash. Normal plasma (Ilex, Italy, 84670-11) and plasma derived from SLE patients (either from Gradipore, Australia, LAHP-1, or from Biopool, Ventura, Calif.) were prepared according to the producer's instruction. The plasma was diluted 1/10 in the blocking buffer and was added to the CL and ethanol coated wells. Binding of NST513 and NST516 compounds to CL was performed by addition of serial dilutions of NST compounds (prepared in the plasma/blocking buffer solution) to the CL or ethanol coated wells. Following 3 hr incubation, the plates were washed twice with PBS/BSA buffer (0.4% bovine serum albumine (BSA) in PBS). For detection of anti cardiolipin binding property of the tested plasma, the plates were incubated with a 1/10000 dilution of Peroxidase-conjugated affinity purified Goat anti-human IgG (Jackson Immunoresearch lab.) in PBS/BSA buffer for 1 hour. The plates were then washed 3 times with PBS/BSA buffer, and color reaction was developed by incubation with 100 ul of 0-phenylenedi-amine (OPD) dihydrochloride (Sigma p-7288) at a concentration of 0.4 mg/ml in 0.05 M phosphate citrate buffer, pH 5.0 supplemented with 4 ul of 30% hydrogen peroxide (Aldrich) for 10 ml mixture. To detect the level of NST500 compounds that were bound to CL, parallel wells were incubated with streptavidin conugated to OPD (SA-OPD, Jackson Immunoresearch lab.), that specifically recognize the biotinylated NST 500 compounds. The resulting colour changes were recorded at 405 nm using a Bio Tek Elx800 Eliza reader.

The results are presented here in FIG. 5A, and demonstrate a competition between NST500 compounds and plasma derived from SLE patients, showing that low concentrations of NST500 can inhibit binding of plasma derived from SLE patients to CL. A dose dependent inhibition of binding of plasma derived from SLE patients (from the commercial source: Biopool, Ventura, Ca USA), to cardiolipin was evident when both compounds were used at concentrations of 1–10 μM. At the lower concentrations of 1 μM, the NST516 compound had a preferred effect over the NST513 compound, lowering the binding of plasma derived from SLE patients to CL by a factor of 2. At this concentration, the NST513 compound still did not exhibit displacement of plasma derived from SLE patients from binding the CL. Thus, NST516 is 10 times more potent than NST513. However, at the higher concentration of 10 μM, both compounds demonstrated almost complete displacement of plasma derived from SLE patients from binding to CL. Therefore, these compounds exhibit an ability to serve as a competitive inhibitor, for binding of plasma derived from SLE patients to PS presenting surfaces.

B. NST500 Compounds Inhibit Binding of Anti β2GPI Antibodies to HUVEC Cells.

Human β2GPI is a plasma phospholipid binding protein that is required for the binding of autoantibodies in sera from patients with APS to cardiolipin (McNeil H P et al., 1990 Proc. Natl. Acad. Sci. 87, 4120–4124). The β2GPI protein binds also to PS presenting cells (Yan W Y et al., 1996, Lupus, 5, 504.) and to activated platelets (Nimpf J E et al., 1987, Biochem. Biophis. Acta, 884, 142), and exhibits anticoagulant properties. Anti β2GPI antibodies are present in sera of APS patients. Therefore, the ability of the NST500 compounds to interfere with the binding of anti βGPI to PS presenting cells was tested in a modified ELISA assay, and is demonstrated here in FIG. 5B. For cell-ELISA tests, HUVEC cells (at 40,000/well), were plated on 96 well tissue culture plates (Nunc) in 200 μl of the culture medium, and allowed to grow for 18–22 hours. Following 2 washes with Hepes buffer (10 mM Hepes pH 8, 140 mM NaCl) and 5 min incubation with the culture medium, the wells were incubated for 3 hr with 10% of normal plasma in PBS (as a source of β2 GPI protein), supplemented with 1/500 of goat anti-human Apolipoprotein-H (β2 GPI) (Affinity biologicals, PA). Parallel control wells were incubated with 10% of normal plasma from Ilex. Serial dilutions of NST500 compounds were prepared in plasma/PBS. Washes and development were as described for anti CL ELISA.

As presented in FIG. 5B, in the presence of plasma and absence of NST500, HUVEC cells supported binding of anti β2GPI to their surface. However, displacement of anti β2GPI by NST500 compounds in this system occurred in a concentration dependent manner, similar to the results obtained with CL. At a concentration of 10 μM, the NST516 compound displayed a better potency than NST513 in displacing anti β2GPI antibodies from HUVEC cell's surface, and its inhibiting activity was two times better than NST513. The linear compound NST512 did not exhibit any inhibitory activity (not shown).

These data therefore demonstrate, that NST500 compounds can serve as a competitive inhibitor for binding of anti β2GPI that is present in sera of SLE patients to physiological surfaces, and lower the pro-thrombotic risks associated with binding of anti phospholipid antibodies to negatively charged surfaces.

Example 5

NST513 Compound can Detect Apoptotic Cells In-Vivo

The assessment of apoptotic processes taking place in vivo, requires direct examination of biopsied or aspirated material. A technique capable of localizing and quantifying apoptosis in vivo would permit assessment of apoptotic-related disease progression or regression and similarly define the efficacy of therapy designed to inhibit or induce cell death.

In order to demonstrate the potential use of NST513 compounds as in-vivo detector of apoptotic process, we have used an animal model of induction of hepatic apoptosis in mice by the anti Fas antibody. The Fas protein, encoded in the mouse by the gene fas, is a cell surface antigen of about 35 kDa that mediates apoptosis (Nagata S et al., 1995, Science 267, 1449–1456) and is expressed in a variety of tissues including liver, heart, lung, ovary, kidney and thymus. Fas has been shown to trigger apoptosis in susceptible target cells when bound to its physiological ligand (FasL) (Suda T. et al., 1994, J Exp. Med. 179, 873–879.), or to agonistic anti-Fas antibodies (Itoh N et al., 1991, Cell 66, 233–234). In-vivo treatment of mice with an anti-Fas monoclonal agonistic antibody induces early and massive apoptosis of hepatocytes, leading to the death of the animal within few hours. The sequence of the pathological changes are similar to those found in acute liver failure due to hepatitis viruses infection or toxins in humans. In the current study, we have used the NST513 compounds and performed immunohistochemical analysis to determine its ability to detect in vivo sites of apoptotic cell death occurring in Fas-mediated hepatocyte apoptosis. Such in vivo studies may prove useful in a clinical setting for noninvasive diagnosis, monitoring of disease progression or regression, and determining efficacy of treatment.

A. Murine Model of Fas-Mediated Apoptosis

Massive hepatic apoptosis can be induced within 1–2 hr in mice following intravenous injection of anti-Fas antibody (Ogasawara J. et al., 1993, Nature, 364, 806–809). We have used this well described model of in-vivo programmed cell death to test the specific localization of NST513 to an organ undergoing apoptosis in vivo. Five-weeks-old male BALB/c mice were injected intravenously with 10 μg/animal of purified hamster anti-Fas mAb (Jo2, PharMingen, San Diego, Calif.) using the model described by Ogasawara et. al. (Nature, 1993, 364, 806–809). Mice were then injected intravenous with 5 μM of NST513. Injections were performed at different time intervals between 5 min–2 hr after antibody treatment. Two different types of control animals were used: animals injected with NST513 only, and animals treated with the anti-Fas antibodies only. All animals were killed 2 hr after administration of antibody followed by organ removal. Heart, lung and liver were collected. Liver were sectioned transversely across the mid-portion of each lobe; organs were fixed in phosphate-buffered formalin for histological and immunohisto-chemical analyses. Severe histological lesions of the liver were observed in treated mice, including morphological changes characteristics of apoptosis (FIG. 6A compared to FIG. 6B). Sections of liver from mice treated with the anti-Fas antibody showed margination of chromatin, pyknosis, and karyorrhexis as well as changes that were focally associated with hemorrhage (peliosis) (FIGS. 6B and 6D) in the entire lobule. Evidence of apoptosis were provided by several parameters: the first is the morphological structure of the cell and nuclei stained with Hematoxylin/Eosin indicating that apoptotic injury has been observed in 80–90% of all hepatocytesas (shown in FIG. 6B) as compared to control non treated animal (shown in FIG. 6A). The second is by the number of TUNEL-positive cells that represented approximately 25% of hepatocytes after 2 hours (FIG. 6D as compared to control animal in FIG. 6C). Example of TUNEL-positive cell is marked by an arrow in FIG. 6D and a TUNEL-negative cell is marked by an arrow in FIG. 6C. The absence of inflammatory cells was consistent with the noninflammatory nature of the apoptotic cell death. No evidence of apoptotic cells was observed when liver sections from control animals injected with NST513 alone were seen (not shown). Similar results were obtained when animals were injected with PBS alone (data not shown). Histological analysis were performed with other organs (heart and lung), and no apoptotic or necrotic cells were observed after injection of the antibody (not shown).

B. Staining of Apoptotic Cells with NST513

Animals that were subjected to induction of apoptosis by the Fas antibody were used for staining with NST513 compound in order to evaluate the ability of this compound to label apoptotic cells in-vivo. Formalin fixed paraffin-embedded tissues were sectioned (5 μm) for staining with Hematoxylin/Eosin or other techniques. Endogenous peroxidase activity was blocked by incubation with 3% $H_2O_2$.

Sections were washed in phosphate buffered saline (PBS) Bound NST513 was visualized using the avidin biotin complex method with horse-radish peroxidase conjugated avidin [DAKO® Catalyzed Signal Amplification (CSA) System, and Peroxidase (# K1500, DAKO corporation, CA USA)] at room temperature. After washing with PBS, staining was developed with 3,3-diaminobenzidine tetrahydrochloride (DAB), and counterstained with Hematoxylin.

For the detection of apoptotic nuclei, sections were stained using the ApopTag® Plus Peroxidase In Situ apoptosis detection kit (#S7101-KIT, Appligene ONCOR, MD USA). Labeling of apoptotic cells is based on modifying genomic DNA using terminal deoxynucleotidyl transferase (TdT), and detection of positive cells is done by specific staining.

Histological Examination

Liver sections from different lobes were used for detection of stained apoptotic cells compared to normal cells. Using light microscopy (×400), twenty fields of stained cells were evaluated. A ratio between the number of stained apoptotic hepatocytes versus stained normal hepatocytes in the field was defined. The stained cell's score (%) corresponds to the mean of the values for the twenty evaluated fields.

The percentage of apoptotic cells in the fields was estimated by evaluating parallel sections stained with Hematoxylin/Eosin. Analysis was performed blindly, since the pathologist performing the histological evaluation was unaware of the assignment of mice to the treatment or control group.

Data Analysis

Histological parameters are presented as mean±SEM. ANOVA with Student-Neuman-Kuels multiple comparison of means test was used to assess the results.

NST513 staining (brown immunostaining product-in the figure is shown as a dark spot) was observed at cytoplasma and cytoplasmatic border of apoptotic hepatocytes (FIGS. 7B and 7D) as compared to sections from animals injected with NST513 only (FIGS. 7A and 7C). Although this result was focal, the localization pattern is consistent with phosphatidylserine (PS) externalization, and staining was never observed in normal hepatocytes (FIGS. 7A and 7C). The same pattern of staining appeared when Annexin V (a protein that strongly binds to PS containing membranes) was exogenously added to the apoptotic cells (data not shown). These experiments indicate that exposure of PS on the surface of cells undergoing apoptosis can be detected in-vivo with the NST513 compound in animal model such as Fas mediated fulminant hepatitis.

C. Time-Course Studies

The time course of in vitro labeling of apoptotic cells by the compound NST513-biotin was examined in the following time intervals: 20, 60, 90, and 120 min after injection of the compound (FIG. 8). The peak of the staining appeared after 60 minutes from injection of the NST513 compound (FIG. 8B), and then slowly declined (FIGS. 8C–8D). Two hours after the injection of the compound, a slight staining was still found (FIG. 8D). To quantitate the microscopic examination of the pharmacokinetics studies, the number of stained cells from 20 microscopic fields was counted. At each time point, the number of apoptotic cells stained with NST513 was counted, as well as the number of non-apoptotic cells. The results are presented in FIG. 9. At 20 min following compound injection, a 3 times increase in the number of apoptotic cells was detected as compared to non specific staining of non-apoptotic cells. The highest ratio (×5 fold) of apotic stained cells was detected 60 min. after compound injection. After this time point, labeling of cells decreased, probably reflecting degradation and clearance of the compound from the liver.

The above results indicate that the NST513 is a suitable compound for diagnostic purposes due to its ability to significantly differentiate apoptotic cells from normal cells and it's convenient time clearance from the detected organs.

$X_4$ consists of 4 amino acids, of which 2 are aromatic amino acids, 1 is a polar uncharged amino acids and 1 is a hydrophobic aliphatic amino acids;

$X_5$ consists of 8 amino acids, of which 4–5 are positively charged and 0–1 is negatively charged, 2 amino acid residues being polar uncharged amino acids, wherein the 2 amino acid residues form a cyclic structure and 1 polar uncharged amino acid;

wherein the groups $X_3$, $X_4$ and $X_5$ being located at various places in the compound;

$X_6$ is a compound of general formula II

The invention claimed is:

1. A compound of general formula I comprising the following components:

$$X_1-X_2-\{(X_3)_a/X_4/X_5\}-X_6$$

wherein:

$X_1$ stands for a saturated or unsaturated fatty acid residue comprising 14 carbon atoms;

$X_2$ is 0;

$X_3$ consists of 1–2 positively charged amino acids;

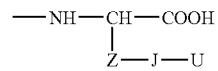

wherein Z stands for a spacer group selected from the group consisting of alkane and alkene containing 1–5 carbon atoms, J stands for a functional group selected from the group consisting of amines, thiols, alcohols, carboxylic acids and esters, aldehydes and alkyl halides; U is 0 or a labeling group for specific binding selected from the group consisting of biotin and a group containing a substituent selected from the group consisting of a fluorescein, a radioisotope and a paramagnetic contrast agent;
wherein:
a stands for an integer of 1–2.

2. The compound according to claim 1, wherein $X_1$ is a myristic acid.

3. The compound according to claim 1, wherein the positively charged amino acids of $X_3$ and $X_5$ are selected from the group consisting of lysine, arginine, histidine and combinations thereof.

4. The compound according to claim 3, wherein the positively charged amino acids of $X_3$ and $X_5$ are selected from the group consisting of lysine, arginine and combinations thereof.

5. The compound according to claim 1 wherein the negatively charged amino acids of $X_5$ are selected from the group consisting of glutamate and aspartate.

6. The compound according to claim 1 wherein the polar uncharged amino acids of $X_5$ are selected from the group consisting of serine, threonine, asparagine, glutamine and combinations thereof.

7. The compound according to claim 1, wherein the aromatic acids of $X_4$ are selected from the group consisting of phenylalanine, tryptophan and combinations thereof.

8. The compound according to claim 1, wherein the polar uncharged amino acid of $X_4$ is selected from the group consisting of serine, asparagine, glutamine and combinations thereof.

9. The compound according to claim 1, wherein the hydrophobic aliphatic amino acid of $X_4$ is selected from the group consisting of leucine, valine, alanine, glycine and combinations thereof.

10. The compound according to claim 1, wherein cyclization of $X_5$ is performed via an intra-molecular disulfide bridge or by an amide bond or via a bond to $^{99}$Tc.

11. The compound according to claim 1, wherein the fluorescein is fluorescein isothiocyanate.

12. The compound according to claim 1, wherein the radioisotope is selected from the group consisting of technetium, lead, mercury, thallium and indium.

13. The compound according to claim 1, wherein the paramagnetic contrast agent is a paramagnetic metal ion chelate gadolinium-diethylenetriaminepentaacetic acid (Gd-DTPA).

14. The compound according to claim 1, wherein $X_6$ is a lysine residue being substituted at an e-amino group by a labeling group.

15. The compound according to claim 1, wherein $X_6$ stands for a cysteine residue bound through a thioether bond to a prenyl group, in which the cysteine carboxyl group is either free or methylated.

16. Myristate-KVSFFCKNKEKKC-K (SEQ ID NO:1)U, wherein U is as defined in claim 1.

17. Myristate-KVSFFCKNKEKKC-K(SEQ ID NO:1) (biotin) in which the two cystein residues are linked via a disulfide bond, to form a cyclic structure.

18. Myristate-KKVFSFCKNKEKKC-K(SEQ ID NO:2) U, wherein U is as defined in claim 1.

19. Myristate-KKVFSFCKNKEKKC-K(SEQ ID NO:2) (biotin) wherein the two cystein residues are linked together.

20. A pharmaceutical composition comprising as active ingredient the compound according to any one of claims 1 to 15.

21. A pharmaceutical composition comprising as active ingredient the compound according to claim 1, which comprises in addition to the NST500 compound a pharmaceutically acceptable carrier.

22. A pharmaceutical composition comprising as active ingredient the compound according to claim 21, wherein the carrier is selected from the group consisting of suitable solvents; emulgators; excipients; and talc.

23. A pharmaceutical composition comprising as active ingredient the compound according to claim 1 which is selected from the group consisting of tablets, capsules, solutions, and emulsions.

24. A pharmaceutical composition comprising as active ingredient the compound according to claim 1 comprising an additional pharmaceutically active compound.

25. A diagnostic kit comprising the compound according to claim 1.

26. A process for the preparation of the compound of the general formula 1 according to claim 1 comprising the following steps:
a. an orthogonally protected diaminoacid is loaded on a solid support, the ω-amino protecting group is then removed, thereafter a compound comprising substituent U being a labeling agent and not standing for 0 is introduced into amino acid resin in the presence of a coupling reagent and a base, or by using a pre-activation method, then removing the α-amino protecting group of the N-terminal amino acid and the peptide being prepared sequentially on the solid support; and, optionally
b. a substituent $X_1$ is introduced into the peptide-resin under similar conditions to those used during the coupling of the amino acids in step a, and then the peptide is cleaved from the solid support.

27. A process according to claim 26, wherein a cyclization of the peptide is performed via an intramolecular di-sulphide bridge by iodine treatment, removal of S-Acm protecting groups on the residues with mercury acetate followed by air oxidation, or by simultaneous de-protection/oxidation with Tl(TFA)$_3$.

28. A process according to claim 26 wherein the cyclization is performed via a coordination bond to a metal.

29. A process according to claim 26, wherein a branched 4-multivalent peptide is prepared in that the fatty acid is coupled to A—Y$_2$, wherein Y is a protecting group of the carboxyl group, the Y protecting group being then removed and the fatty acid-A being coupled with two equivalents of A—Y$_2$, the Y group being then removed and the skeleton obtained being then coupled with a protected peptide prepared on a solid support the final skeleton peptide being purified, lyophilized and characterized by HPLC/MS.

30. A process according to claim 26 or 29, wherein a branched 8-multivalent peptide is prepared in that the fatty acid

is then coupled with two equivalents of A—(Y)$_2$ and then the Y protecting groups are removed, the skeleton then being coupled with four equivalents of A—(Y)$_2$ and the process being continued octavalent peptide.

* * * * *

SEQUENCE LISTING

```
<160> NUMBER OF SEQ ID NOS: 3

<210> SEQ ID NO 1
<211> LENGTH: 14
<212> TYPE: PRT
<213> ORGANISM: Artificial
<220> FEATURE:
<223> OTHER INFORMATION: Description of Artificial Sequence:  Synthetic
      Peptides

<400> SEQUENCE: 1

Lys Val Ser Phe Phe Cys Lys Asn Lys Glu Lys Lys Cys Lys
1               5                   10

<210> SEQ ID NO 2
<211> LENGTH: 15
<212> TYPE: PRT
<213> ORGANISM: Artificial
<220> FEATURE:
<223> OTHER INFORMATION: Description of Artificial Sequence:  Synthetic
      Peptides

<400> SEQUENCE: 2

Lys Lys Val Phe Ser Phe Cys Lys Asn Lys Glu Lys Lys Cys Lys
1               5                   10                  15

<210> SEQ ID NO 3
<211> LENGTH: 14
<212> TYPE: PRT
<213> ORGANISM: Artificial
<220> FEATURE:
<223> OTHER INFORMATION: Description of Artificial Sequence:  Synthetic
      Peptides

<400> SEQUENCE: 3

Lys Val Ser Phe Phe Cys Lys Asn Lys Lys Lys Lys Cys Lys
1               5                   10
```